(12) United States Patent
Hall et al.

(10) Patent No.: US 7,582,436 B2
(45) Date of Patent: Sep. 1, 2009

(54) 3' END TAGGED OLIGONUCLEOTIDES

(75) Inventors: Jeff G. Hall, Madison, WI (US); Zbigniev Skrzypczynski, Verona, WI (US); Sarah Wayland, Madison, WI (US); Ned D. Reimer, Madison, WI (US); Luis P. Reynaldo, Madison, WI (US); Joerg Baier, Verona, WI (US); Victor Lyamichev, Madison, WI (US); Bruce P. Neri, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 160 days.

(21) Appl. No.: 11/787,843

(22) Filed: Apr. 18, 2007

(65) Prior Publication Data

US 2008/0293930 A1 Nov. 27, 2008

Related U.S. Application Data

(62) Division of application No. 10/350,620, filed on Jan. 24, 2003, now abandoned.

(51) Int. Cl.
*C12Q 1/68* (2006.01)
*C07H 21/00* (2006.01)

(52) U.S. Cl. .......................... 435/6; 536/22.1
(58) Field of Classification Search ............. 435/6; 536/22.1
See application file for complete search history.

(56) References Cited

U.S. PATENT DOCUMENTS

| 5,256,549 A | * | 10/1993 | Urdea et al. ............... 435/91.1 |
| 5,614,402 A | | 3/1997 | Dahlberg et al. |
| 5,795,763 A | | 8/1998 | Dahlberg et al. |
| 5,843,669 A | | 12/1998 | Kaiser et al. |
| 5,846,717 A | | 12/1998 | Brow et al. |
| 5,985,557 A | | 11/1999 | Prudent et al. |
| 5,994,069 A | | 11/1999 | Hall et al. |
| 6,001,567 A | | 12/1999 | Brow et al. |
| 6,090,543 A | | 7/2000 | Prudent et al. |
| 6,090,606 A | | 7/2000 | Kaiser et al. |
| 6,194,149 B1 | | 2/2001 | Neri et al. |
| 6,472,522 B1 | * | 10/2002 | Horn et al. ................ 536/25.4 |

FOREIGN PATENT DOCUMENTS

| WO | WO 97/27214 | 7/1997 |
| WO | WO 98/23774 | 6/1998 |
| WO | WO 98/42873 | 10/1998 |
| WO | WO 98/50403 | 11/1998 |
| WO | WO 01/90337 | 11/2001 |
| WO | WO 01/98537 | 12/2001 |
| WO | WO 02/070755 | 9/2002 |

OTHER PUBLICATIONS

Lyamichev et al., Nat. Biotech., 17:292 (1999).
Hall et al., PNAS, USA, 97:8272 (2000).
de Arruda et al., Expert Rev. Mol. Diagn., 2(5), 487-496 (2002).
Horn et al. (1988) in Nucleic Acids Res. 16:11559-11571.
Kwiatkowski et al. (1996) Nucleic Acids Res. 24:4632-4638.

* cited by examiner

*Primary Examiner*—Suryaprabha Chunduru
(74) *Attorney, Agent, or Firm*—Casimir Jones, S.C.

(57) ABSTRACT

The present invention provides compositions comprising oligonucleotides that have 3' end groups (e.g. lipophilic moieties) that are useful in invasive cleavage reactions such as the INVADER assay. Specifically, the present invention provides compositions containing oligonucleotides with 3' end groups configured for generating a detectable signal in invasive cleavages assays with a high signal-to-background ratio, as well as methods for generating such compositions.

6 Claims, 20 Drawing Sheets

A

B

C

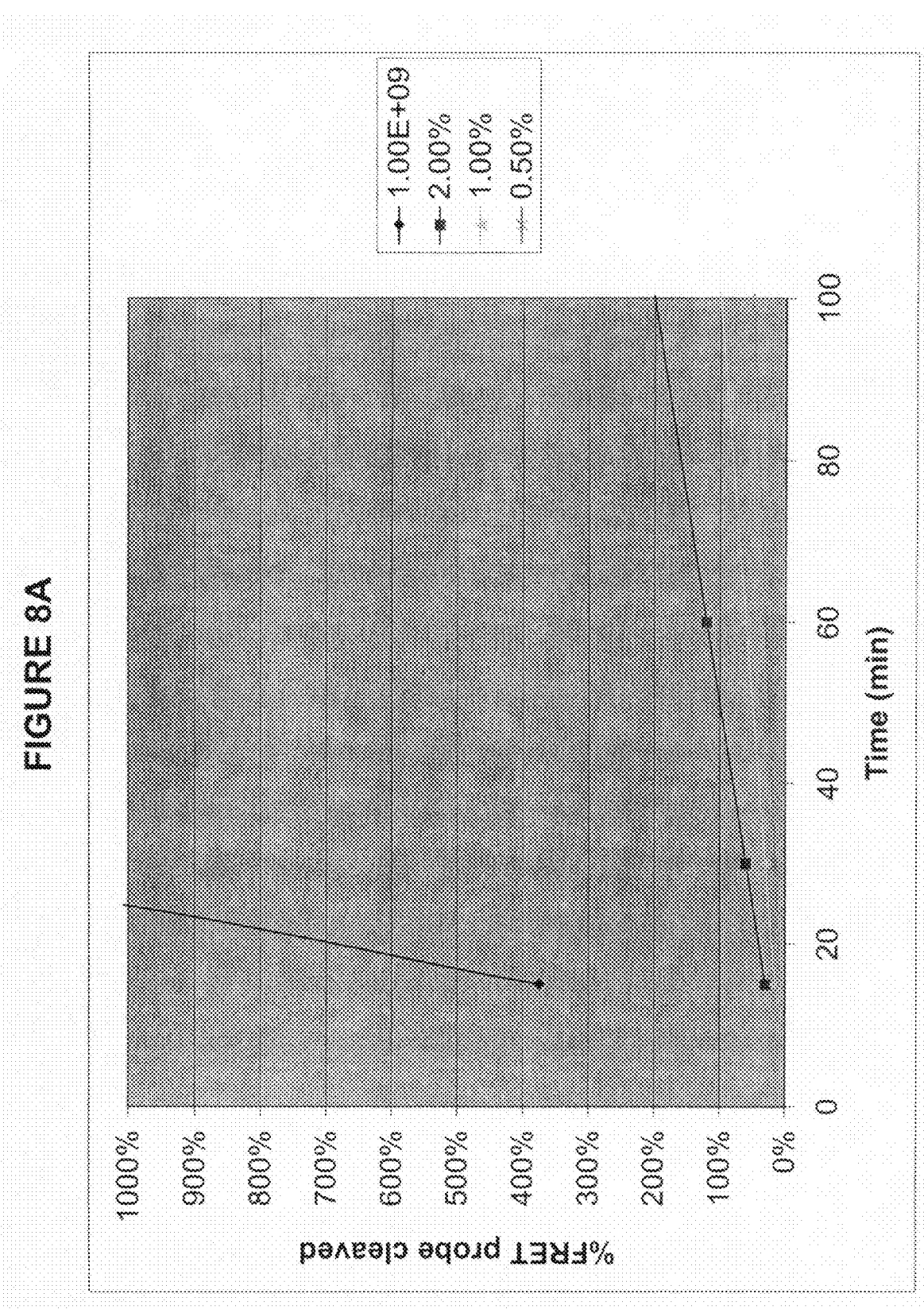

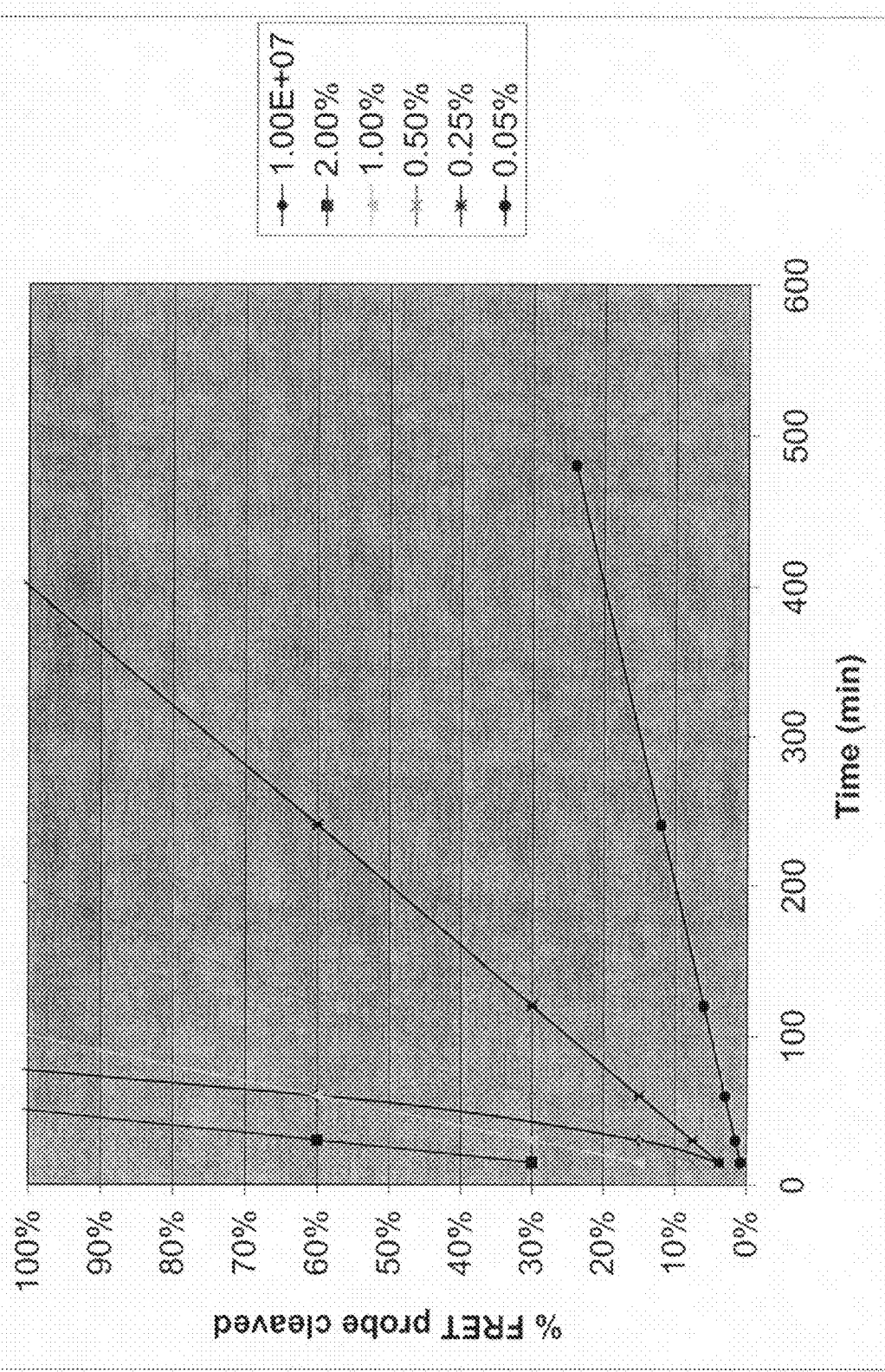

3' END TAGGED OLIGONUCLEOTIDES

The present invention is a divisional application of U.S. application Ser. No. 10/350,620, filed Jan. 24, 2003 now abandoned, which is incorporated herein by reference in its entirety.

FIELD OF THE INVENTION

The present invention relates to tagged oligonucleotides that have 3' end groups that are useful in invasive cleavage reactions such as the INVADER assay. Specifically, the present invention relates to compositions containing oligonucleotides with lipophilic 3' end groups configured for generating a detectable signal in invasive cleavage assays with a high signal-to-background ratio, as well as methods for generating such compositions.

BACKGROUND OF THE INVENTION

With the completion of the Human Genome Project and the increasing volume of genetic sequence information available, genomics research and subsequent drug design efforts have been increasing as well. Many diagnostic assays and therapeutic methods utilize oligonucleotides. The information obtained from genomic analysis provides valuable insight into the causes and mechanisms of a large variety of diseases and conditions, while oligonucleotides can be used to alter gene expression in cells and tissues to prevent or attenuate diseases or alter physiology. As more nucleic acid sequences continue to be identified, the need for larger quantities of oligonucleotides used in assays and therapeutic methods increases. As such, what is needed are compositions and methods for cost-efficient production of oligonucleotides of sufficient purity for use in nucleic acid detection assays, such as invasive cleavage structure assays (e.g. the INVADER assay).

SUMMARY OF THE INVENTION

The present invention provides compositions comprising oligonucleotides that have 3' end groups (e.g. lipophilic moieties) that are useful in invasive cleavage reactions such as the INVADER assay. Specifically, the present invention provides compositions containing oligonucleotides with 3' end groups configured for generating a detectable signal in invasive cleavage assays with a high signal-to-background ratio, as well as methods for generating such compositions. In certain embodiments, the 3' end groups are affinity groups.

In some embodiments, the present invention provides compositions comprising a plurality of tagged oligonucleotides, wherein the tagged oligonucleotides comprise a lipophilic 3' end group, and wherein the tagged oligonucleotides are configured to be cleaved by structure-specific enzymes in a first invasive cleavage reaction such that fragments are generated, wherein the fragments are configured to participate in a second invasive cleavage reaction in order to generate a detectable signal. In some embodiments, the tagged oligonucleotides are configured to serve as probe oligonucleotides (downstream oligonucleotides) in the first invasive cleavage reaction (see FIG. 1). In other embodiments, the fragments are configured to serve as INVADER oligonucleotides (upstream oligonucleotides) in the second invasive cleavage reaction.

In particular embodiments, the second invasive cleavage assay comprises a FRET cassette, and the fragments are configured to hybridize to the FRET cassette. In other embodiments, the oligonucleotides are at least 20 nucleotides in length (e.g. 20-35 bases in length). In certain embodiments, the fragments are about 10 to about 15 bases in length (e.g. 8-17 bases in length).

In other embodiments, the present invention provides compositions comprising a plurality of tagged oligonucleotides, wherein the tagged oligonucleotides comprise a lipophilic 3' end group, wherein the lipophilic 3' end group comprises a long-chain polycarbon linker. In certain embodiments, the oligonucleotides of the present invention further comprise a 5' end group (e.g. to facilitate purification).

In additional embodiments, the present invention provides compositions comprising a plurality of tagged oligonucleotides, wherein the tagged oligonucleotides comprise a lipophilic 3' end group, and wherein the tagged oligonucleotides further comprise a 5' portion and a 3' portion, wherein the 3' portion is configured to hybridize to a target sequence, and wherein the 5' portion is configured to not hybridize to the target sequence. In certain embodiments, the oligonucleotides are configured to be cleaved in an invasive cleavage assay such that a fragment is generated, wherein the fragment contains the 5' portion of the oligonucleotide and one additional nucleotide from the 3' portion of the oligonucleotide.

In particular embodiments, the lipophilic 3' end group comprises a long-chain polycarbon linker (e.g. $C_{14}$, $C_{15}$, $C_{16}$, $C_{17}$, $C_{18}$, $C_{19}$, etc.). In some embodiments, the lipophilic 3' end group is selected from an aliphatic linear hydrocarbon or derivative thereof, a branched hydrocarbon or derivative thereof, an aromatic hydrocarbon or derivative thereof, and a polyaromatic hydrocarbon or derivative thereof. In certain embodiments, the lipophilic 3' end group introduces sufficient lipophilic character to allow an attached oligonucleotide to be retained on a lipophilic purification device, but not so much lipophilic character that it is difficult to remove the molecules from the purification device or to maintain the molecules in solution.

In certain embodiments, the detectable signal generated by the plurality of tagged oligonucleotides in the compositions of the present invention provides at least a 1.75 signal-to-background ratio in a biological detection assay (e.g., an INVADER assay). In other embodiments, the plurality of tagged oligonucleotides contain an intact 3' end and are free from abasic sites. In certain embodiments, the abasic sites are selected from apurinic sites and apyrimidinic sites. In some embodiments, the compositions of the present invention contain less than 0.01% of shrapnel molecules (e.g., in invasive cleavage assays, the compositions contain less than 0.01% of un-tagged oligonucleotide fragments capable of generating a detectable signal in the second invasive cleavage reaction without first being cleaved by forming a specific substrate for the cleavage agent in the first invasive cleavage assay). In other embodiments, the compositions of the present invention contain less than 0.1% of shrapnel molecules. In certain embodiments, the compositions are configured to generate the detectable signal when combined with about $10^4$ target sequences (e.g. the composition comprises 0.01% or less of shrapnel and is configured to generate the detectable signal when combined with genomic DNA). In other embodiments, the compositions are configured to generate the detectable signal when combined with about $10^6$ target sequences (e.g. the composition comprises 0.1% or less of shrapnel). In some embodiments, the compositions are configured to generate the detectable signal when combined with about $10^7$ target sequences (e.g. the composition comprises 4.0%, or 3.0% or 2.0% or less of shrapnel).

The present invention also provides compositions comprising: a) a solid support (e.g. CPG), b) a lipophilic moiety attached to the solid support, and c) an oligonucleotide comprising a 3' end and a 5' end, wherein the 3' end is attached to the lipophilic moiety, and wherein the oligonucleotide is configured to be cleaved by structure-specific enzymes in a first invasive cleavage reaction such that a fragment is generated, wherein the fragment is configured to participate in a second invasive cleavage reaction in order to generate a detectable signal. In certain embodiments, the second invasive cleavage assay comprises a FRET cassette, and the fragment is configured to hybridize to the FRET cassette. In some embodiments, the oligonucleotide is configured to serve as a probe oligonucleotide (downstream oligonucleotide) in the first invasive cleavage reaction (see FIG. 1). In other embodiments, the fragment is configured to serve as an INVADER oligonucleotides (upstream oligonucleotides) in the second invasive cleavage reaction.

In other embodiments, the present invention provides compositions comprising: a) a solid support (e.g. CPG), b) a lipophilic moiety attached to the solid support, wherein the lipophilic moiety comprises a long-chain polycarbon linker, and c) an oligonucleotide comprising a 3' end and 5' end, wherein the 3' end is attached to the lipophilic moiety. In certain embodiments, the present invention provides compositions comprising: a) a solid support (e.g. CPG), b) a lipophilic moiety attached to the solid support, and c) an oligonucleotide comprising a 3' end and 5' end, wherein the 3' end is attached to the lipophilic moiety, and wherein the oligonucleotide further comprises a 5' portion and a 3' portion, wherein the 3' portion is configured to hybridize to a target sequence, and wherein the 5' portion is configured to not hybridize to the target sequence.

In some embodiments, the lipophilic moiety comprises a long-chain polycarbon linker. In particular embodiments, the lipophilic moiety comprises a long-chain polycarbon linker (e.g. $C_{14}$, $C_{15}$, $C_{16}$, $C_{17}$, $C_{18}$, $C_{19}$, $C_{20}$, etc.). In some embodiments, the lipophilic moiety is selected from an aliphatic linear hydrocarbon or derivative thereof, a branched hydrocarbon or derivative thereof, an aromatic hydrocarbon or derivative thereof, and a polyaromatic hydrocarbon or derivative thereof. In certain embodiments, the lipophilic moiety introduces sufficient lipophilic character to allow an attached oligonucleotide to be retained on a lipophilic purification device, but not so much lipophilic character that it is difficult to remove the molecules from the purification device or to maintain the molecules in solution.

In certain embodiments, the present invention provides methods of synthesizing oligonucleotides, comprising; a) providing a solid support comprising a plurality of affinity groups, b) synthesizing a plurality of oligonucleotides in the 3' to 5' direction such that the 3' ends of the oligonucleotides are attached to the affinity groups, wherein the oligonucleotides are configured to be cleaved by structure-specific enzymes in a first invasive cleavage reaction such that fragments are generated, wherein the fragments are configured to participate in a second invasive cleavage reaction in order to generate a detectable signal.

In other embodiments, the present invention provides methods of synthesizing oligonucleotides, comprising; a) providing a solid support comprising a plurality of affinity groups, wherein the affinity groups comprise long-chain polycarbon linkers, b) synthesizing a plurality of oligonucleotides in the 3' to 5' direction such that the 3' ends of the oligonucleotides are attached to the affinity groups. In certain embodiments, the synthesizing occurs in a nucleic acid synthesizer (e.g. ABI 3900 synthesizer, NEI-48, or similar devices).

In particular embodiments, the methods of the present invention further comprise a step of treating the oligonucleotides with an agent (e.g. aqueous lysine) such that abasic sites in the oligonucleotides are cleaved while the 3' ends of the oligonucleotides remain attached to the solid support via the affinity groups. In other embodiments, the methods of the present invention further comprise a step of cleaving the oligonucleotides from the solid support to generate a plurality of cleaved oligonucleotides comprising 3' end affinity groups (e.g. lipophilic moieties).

In yet other embodiments, the present invention further comprises a step of purifying the plurality of cleaved oligonucleotides employing the 3' end affinity groups to generate a plurality of purified oligonucleotides. In some embodiments, the purifying employs a lipophilic purification device. In certain embodiments, the purification device is a column or a cartridge containing solid material possessing specific properties. In particular embodiments, the purifying employs affinity chromatography. In additional embodiments, the affinity chromatography employs an OASIS HLB column. In other embodiments, the affinity chromatography employs a SUPERPURE PLUS column. In still other embodiments, the affinity chromatography employs a TOP CARTRIDGE. In certain embodiments, the detectable signal generated by the plurality of oligonucleotides (e.g. cleaved and/or purified) provides at least a 1.75 signal-to-background ratio in a biological detection assay (e.g., an INVADER assay). In other embodiments, at least 99.9% of the plurality of oligonucleotides are free from abasic sites (e.g. at least 99.99% or at least 99.999% of the plurality of tagged oligonucleotides are free from abasic sites). In certain embodiments, the abasic sites are selected from apurinic sites and apyrimidinic sites. In some embodiments, the compositions of the present invention contain less than 0.1% of shrapnel molecules.

In some embodiments, the solid support comprises CPG. In other embodiments, the solid support comprises polystyrene. In certain embodiments, the polystyrene is non-swellable polystyrene. In other embodiments, the solid supports are located in synthesis columns. In particular embodiments, the synthesis columns are located in a nucleic acid synthesizer (e.g. ABI 3900, NEI-48, or similar devices).

In certain embodiments, the plurality of affinity groups comprises lipophilic moieties. In other embodiments, the lipophilic moieties comprise a long-chain polycarbon linker.

In particular embodiments, the present invention provides methods of synthesizing and purifying oligonucleotides comprising; a) synthesizing a plurality of oligonucleotides on a solid support in the 3' to 5' direction, b) purifying said oligonucleotides based on the presence of a particular 3' end sequence (e.g. the particular 3' end sequence comprises poly A, and the oligonucleotides are passed over an oligo-dT column).

In some embodiments, the present invention provides kits comprising: a) a first oligonucleotide, wherein the first oligonucleotide comprises a lipophilic 3' end group, and b) a second oligonucleotide configured to form an invasive cleavage structure in combination with the first oligonucleotide and a target sequence. In particular embodiments, the lipophilic 3' end group comprises a long-chain polycarbon linker. In certain embodiments, the lipophilic 3' end group is selected from an aliphatic linear hydrocarbon or derivative thereof, a branched hydrocarbon or derivative thereof, an aromatic hydrocarbon or derivative thereof, and a polyaromatic hydrocarbon or derivative thereof. In some embodiments, the 3' end group is at least partially resistant to cleavage such that abasic sites (e.g. apurinic sites) may be cleaved and removed following synthesis (but intact oligonucleotides remain attached to the solid support to allow purification prior from removal from the solid support).

DEFINITIONS

Figure 1:
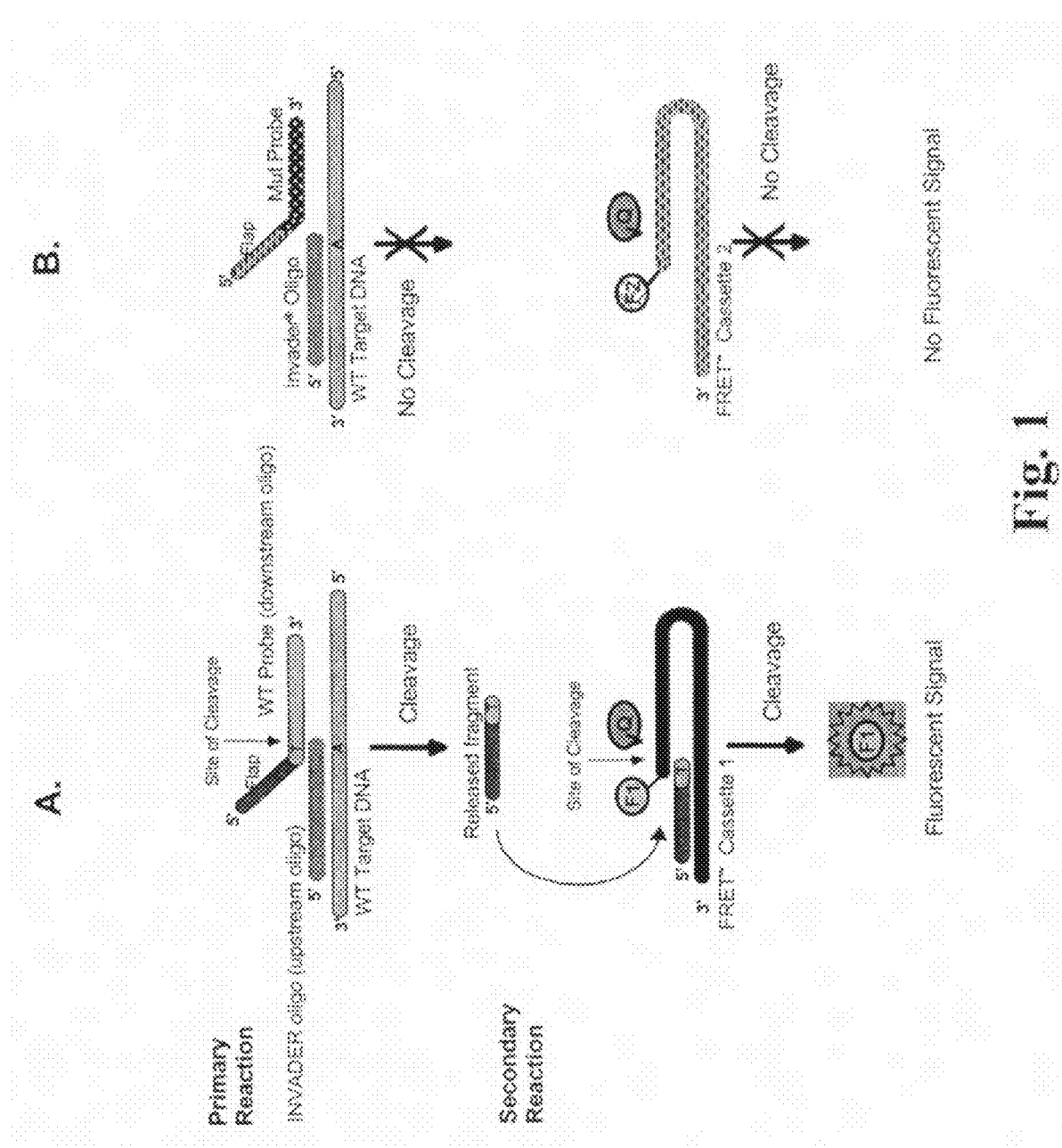
FIG. 1 shows a schematic diagram of a biplex INVADER assay.

To facilitate an understanding of the invention, a number of terms are defined below.

As used herein, the term "nucleic acid synthesis column" or "synthesis column" refers to a container in which nucleic acid synthesis reactions are carried out. For example, some synthesis columns referred to as "cartridges" include plastic cylindrical columns and pipette tip formats, containing openings at the top and bottom ends. The containers may contain or provide one or more matrices, solid supports, and/or synthesis reagents necessary to carry out chemical synthesis of nucleic acids. For example, in some embodiments of the present invention, synthesis columns contain a solid support matrix on which a growing nucleic acid molecule may be synthesized.

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 3' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., Mn2+ and/or Mg2+ ions). Individual ingredients (e.g., oligonucleotides, enzymes, buffers, target nucleic acids) that collectively make up INVADER assay reagents are termed "INVADER assay reagent components".

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more of the INVADER assay reagents may be provided in a predispensed format (e.g., premeasured for use in a step of the procedure without re-measurement or re-dispensing). In some embodiments, selected INVADER assay reagent components are mixed and predispensed together. In other embodiments. In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention (e.g. primary probe oligonucleotides with lipophilic 3' end groups). For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a subset of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides with 3' end group, control target oligonucleotides, etc.).

The term "label" as used herein refers to any atom or molecule that can be used to provide a detectable (preferably quantifiable) effect and that can be attached to a nucleic acid or protein. Labels include but are not limited to dyes; radiolabels such as $^{32}$P; binding moieties such as biotin; haptens such as digoxygenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "oligonucleotide" and "polynucleotide" are used interchangeably, both referring to molecules comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, the terms "complementary" or "complementarity" are used in reference to nucleic acid sequences (e.g. oligonucleotides and target nucleic acid) polynucleotides related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The terms "homology" and "homologous" refer to a degree of identity. There may be partial homology or complete homology. A partially homologous sequence is one that is less than 100% identical to another sequence.

As used herein, the terms "hybridize" and "hybridization" are used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the $T_m$ value may be calculated by the equation: $T_m = 81.5 + 0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of Tm.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full-length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage agent, including but not limited to an enzyme. The cleavage structure is a substrate for specific cleavage by the cleavage agent in contrast to a nucleic acid molecule that is a substrate for non-specific cleavage by agents such as phosphodiesterases which cleave nucleic acid molecules without regard to secondary structure (i.e., no formation of a duplexed structure is required).

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cleavage means" or "cleavage agent" as used herein refers to any agent that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures (e.g. invasive cleavage structure); it is not necessary that the cleavage means cleave the cleavage structure at any particular location within the cleavage structure.

The cleavage agent may include nuclease activity provided from a variety of sources including the CLEAVASE enzymes (Third Wave Technologies, Madison, Wis.), the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use with the present invention are provided in U.S. Pat. Nos. 5,614,402; 5,795,763; 5,843,669; 6,090; PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means). For example, a 5' fragment may be generated when the downstream ICS oligonucleotide in an invasive cleavage structure is cleaved by a structure specific enzyme such a CLEAVASE enzyme.

The terms "target nucleic acid" and "target sequence" refer to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein, the term "purified" or "to purify" refers to the removal of contaminants from a sample. For example, recombinant Cleavase nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n–1).

The term "nucleic acid sequence" as used herein refers to an oligonucleotide, nucleotide or polynucleotide, and fragments or portions thereof, and to DNA or RNA of genomic or synthetic origin which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As used herein, the term "affinity group" refers to any moiety that will bind, adsorb, hybridize, or otherwise attach to a particular binding partner. Affinity groups may attached to particular molecules such that these molecules can be separate from other molecules using the affinity of the affinity group for their binding partners. Examples of affinity groups include, but are not limited to, lipophilic moieties, avidin, biotin, nucleic acid sequences, antibodies or fragments thereof, etc.

As used herein, the term "lipophilic moiety" refers to any molecule with an affinity for lipids. Examples of lipophilic moieties include, but are not limited to, aliphatic linear hydrocarbon or derivative thereof, a branched hydrocarbon or derivative thereof, an aromatic hydrocarbon or derivative thereof, and a polyaromatic hydrocarbon or derivative thereof. Other examples include, but are not limited to, long-chain polycarbon linkers, a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety.

As used herein, the term "long-chain polycarbon linker" refers to a linear aliphatic chain with at least 12 carbon atoms (e.g. C12, C13, C14, C15, . . . C20, etc.). In preferred embodiments, a long-chain polycarbon linker comprises at least 14 carbon atoms.

As used herein, the term "3' end group" refers to any molecule (e.g. affinity group, lipophilic group, etc.) that is attached to the 3' end of an oligonucleotide.

As used herein, an oligonucleotide is said to be "tagged" when an additional, non-nucleotide molecule is attached to the oligonucleotide (e.g. at the 5' end or 3' end of the oligonucleotide).

As used herein, the term "shrapnel" and "shrapnel molecules" in invasive cleavage assays, refers to un-tagged oligonucleotide fragments capable of generating a detectable signal in a second invasive cleavage reaction (e.g. will hybridize with a FRET cassette) without first being cleaved by forming a specific substrate for the cleavage agent in a first invasive cleavage assay. In general, shrapnel molecules contain a functional portion of the downstream oligonucleotide (e.g. the "flap" plus a number of additional bases), but are missing a significant portion of the 3' region of the downstream oligonucleotide. Shrapnel may cause high levels of background signal in cleavage assays, such as the INVADER BIPLEX assay (see FIG. 1) as the shrapnel molecules may be cleaved in the secondary reaction without first being cleaved in the primary reaction (thus generating a detectable signal regardless of the presence of the target DNA or RNA).

DESCRIPTION OF THE INVENTION

The present invention provides compositions comprising oligonucleotides that have 3' end groups (e.g. lipophilic moieties) that are useful in invasive cleavage reactions such as the INVADER assay. The present invention allows cost-efficient production of probe oligonucleotides of sufficient purity for use in, for example, invasive cleavage assays, such as the INVADER assay. Importantly, the present invention provides methods of synthesizing oligonucleotides such that HPLC purification methods do not have to be employed. The present invention also allows oligonucleotides to be synthesized such that the resulting oligonucleotides comprise 3' end groups (e.g. lipophilic moieties) that facilitate purification. Furthermore, the 3' end tagged oligonucleotides of the present invention do not require removal of the 3' end group prior to use in invasive cleavage assays (e.g. INVADER) thus saving time and money in the manufacturing process. Finally, the present invention provides methods of purifying oligonucleotides such that partial sequences likely to interfere in invasive cleavage assays are removed (e.g. shrapnel sequences are removed).

A. Invasive Cleavage Assays

The present invention provides methods and compositions for generating 3' tagged probe oligonucleotides useful in invasive cleavage reactions, such as the INVADER assay. The probe oligonucleotides of the present invention can form a nucleic acid cleavage structure that is dependent upon the presence of a target nucleic acid which can be cleaved so as to release distinctive cleavage products (e.g. fragments, see FIG. 1). 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, an invasive cleavage reaction can occur. Through the interaction of a cleavage agent (e.g., a 5' nuclease) and the INVADER oligonucleotide (upstream oligonucleotide), the cleavage agent can be made to cleave the probe oligonucleotide (downstream oligonucleotide) at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes). One example of an INVADER assay (biplex assay) is shown in FIG. 1.

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 6,090,543; 5,994,069; Lyamichev et al., Nat. Biotech., 17:292 (1999), Hall et al., PNAS, USA, 97:8272 (2000), de Arruda et al., Expert Rev. Mol. Diagn., 2(5), 487-496 (2002), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes (fragments) then direct cleavage of a second labeled probe (i.e. the fragment serves as the INVADER oligonucleotide, and the second labeled probe serves as the downstream probe, and may optionally also provide the target sequence). The secondary probe oligonucleotide can be 5'-end labeled with a fluorophore that is quenched by an internal dye. Upon cleavage, the de-quenched fluorophore-labeled product may be detected using a standard fluorescence plate reader.

The INVADER assay detects specific mutations and SNPs in un-amplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping invasive cleavage structure. An unpaired "flap" (5' portion) is included on the 5' end of the WT primary probe (with the rest of the probe being referred to as the 3' portion or target specific region or TSR). A structure-specific enzyme (e.g. the CLEAVASE enzyme, Third Wave Technologies) recognizes the overlap and cleaves off the unpaired flap and one or more bases from the TSR (depending on the amount of overlap caused by the 3' portion of the INVADER oligonucleotide), releasing a "fragment" as a target-specific product. In the secondary reaction, this cleaved fragment serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the Mut primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA or RNA being detected. The target nucleic acid is the limiting component in the first invasive cleavage, since the INVADER oligonucleotide and primary probe are supplied in molar excess. In the second invasive cleavage, it is the released fragment that is limiting. When these two cleavage reactions are performed sequentially, the fluorescence signal from the composite reaction accumulates linearly with respect to the amount of target nucleic acid.

In certain embodiments, the INVADER assay, or other nucleotide detection assays, are performed with accessible site designed oligonucleotides (e.g. 3' end labeled) and/or bridging oligonucleotides (e.g 3' end labeled). Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197, 557, issued Mar. 6, 2001, and in PCT application WO 98/39485, each incorporated by reference herein in their entireties for all purposes.

In some embodiments, the present invention provides methods for detecting a target sequence, comprising: providing a) a sample containing DNA (e.g. amplified by extension of 3' ends in nicked double-stranded genomic DNA), said genomic DNA suspected of containing said target sequence; b) oligonucleotides (e.g. at least one of which comprises a 3' end group) capable of forming an invasive cleavage structure in the presence of said target sequence; and c) exposing the sample to the oligonucleotides and an agent. In some embodiments, the agent comprises a cleavage agent. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product. In some preferred embodiments, the target sequence comprises a first region and a second region, said second region downstream of and contiguous to said first region, and said oligonucleotides comprise first and second oligonucleotides, said wherein at least a portion of said first oligonucleotide (downstream oligonucleotide) is completely complementary to said first portion of said target sequence and wherein said second oligonucleotide (upstream oligonucleotide) comprises a 3' portion and a 5' portion, wherein said 5' portion is completely complementary to said second portion of said target nucleic acid.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase (as described, e.g., in U.S. Pat. Nos. 5,198, 543 and 5,001,050, each herein incorporated by reference in their entireties for all purposes) in combination with exonuclease-resistant random primers, such as hexamers.

In some embodiments, the present invention provides methods for detecting a target sequence, comprising: providing a) a sample containing DNA amplified by extension of multiple primers on genomic DNA, said genomic DNA suspected of containing said target sequence; b) oligonucleotides (e.g. at least one of which comprises a 3' end group) capable of forming an invasive cleavage structure in the presence of said target sequence; and c) exposing the sample to the oligonucleotides and the agent. In some embodiments, the agent comprises a cleavage agent. In some preferred embodiments, said primers are random primers. In particularly preferred embodiments, said primers are exonuclease resistant. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product. In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

Other modifications may be employed to alter other aspects of oligonucleotide performance in an assay. For example, the use of base analogs or modified bases can alter enzyme recognition of the oligonucleotide. Such modifications may comprise modifications to any portion or portions of a nucleotide, including but not limited to a base moiety, a sugar moiety or a phosphate group, and may comprise addition of, deletion of, and/or substitution of one or more atoms or groups of atoms (e.g., side or R groups) of the nucleotide. In some embodiments, such modifications are used to protect a region of an oligonucleotide from nuclease cleavage. In other embodiments, such modifications are used to alter the interaction between an enzyme and a nucleic acid structure comprising the modification (e.g., alter the binding to, or activity on the structure by the enzyme).

In some embodiments, modifications are used to affect the ability of an oligonucleotide to participate as a member of a cleavage structure that is not in a position to be cleaved (e.g., to serve as an INVADER oligonucleotide to enable cleavage of a probe). Such modifications may be referred to as "blocker" or "blocking" modifications. In some embodiments, assay oligonucleotides incorporate 2'-O-methyl modifications. In other embodiments, assay oligonucleotides incorporate 3' terminal modifications [e.g., $NH_2$; 3' hexanol; 3' hexanediol; 3' phosphate; 3' biotin; PMC, i.e. 3-(P-methoxyphenyl) 1,2 propanediol]. In some embodiments, the blocking modifications are aliphatic linear hydrocarbons, e.g. $C_{12}$, $C_{14}$, or $C_{16}$ linkers. While any modification that can be attached to the 3' terminus of an oligonucleotide, either directly during synthesis or post-synthetically, may be contemplated for use as a blocker, some modifications may be less suitable based on their effects on INVADER assay performance. The suitability of a given 3' terminal oligonucleotide modification may be evaluated by many methods, including, but not limited to:

(a) synthesizing the oligonucleotide;
(b) incorporating the modification;
(c) using the modified oligonucleotide in as a probe oligonucleotide in a standard INVADER assay on all of the following:
  (i) a complementary target
  (ii) a largely complementary target that contains a polymorphism at the nucleotide corresponding to position 1 in the probe oligonucleotide
  (iii) no target
(d) comparing signal generated in (c) to that generated in a standard INVADER assay on i-iii in which the probe oligonucleotide contains one of the following terminal modifications: e.g., $NH_2$; 3' hexanol; 3' hexanediol; 3' phosphate; 3' biotin; PMC, i.e. 3-(P-methoxyphenyl) 1,2 propanediol. Comparison of the signals generated using the candidate blocker modification to the established blocker modification will reveal whether the candidate results in more background signal generation and/or reduced target-dependent signal generation in an INVADER assay. Depending on the extent to which background and/or target-dependent signal is affected by the modification, it may be judged to be better than, equivalent to, or worse than other modifications suitable for use as blockers.

B. Oligonucleotide Synthesis and Purification

The present invention provides improved methods for synthesizing and purifying oligonucleotides (e.g. primary probe oligonucleotides) that contain a 3' end group, such as a lipophilic moiety. In certain embodiments, the 3' end group is an affinity group that allows the oligonucleotides to be purified based on affinity chromatography or similar means.

The present invention is not limited by the means of oligonucleotide synthesis, or the manner in which the 3' end group is attached to the oligonucleotide. In certain embodiments, the 3' end group is attached to the oligonucleotide after synthesis is complete. In preferred embodiments, the oligonucleotide is synthesized starting at the 3' end group. For example, automated nucleic acid synthesizers may be employed, employing solid supports (e.g. CPG) that are attached to the 3' end group. Synthesis can then proceed in the 3' to 5' direction starting at the 3' end group. In preferred embodiments, standard phosphoramidite synthesis methods are employed.

Any type of oligonucleotide synthesis may be employed to generate oligonucleotides, including cloning nucleic acid sequences and automated synthesis using nucleic acid synthesizers. A number of references describe methods of synthesis which may be employed with the method of the present invention. References that relate generally to methods for synthesizing oligonucleotides include those related to 5'-to-3' syntheses based on the use of beta.-cyanoethyl phosphate protecting groups, e.g., de Napoli et al. (1984) Gazz. Chim. Ital. 114:65, Rosenthal et al. (1983) Tetrahedron Lett. 24:1691, Belagaje et al. (1977) Nucl. Acids Res. 10:6295 (all of which are incorporated herein by reference), and those references that describe solution-phase 5'-to-3' syntheses, such as Hayatsu et al. (1957) J. Am. Chem. Soc. 89:3880, Gait et al. (1977) Nucl. Acids Res. 4:1135, Cramer et al. (1968) Angew. Chem. Int. Ed. Engl. 7:473, and Blackburn et al. (1967) J. Chem. Soc. Part C, 2438 (all of which are incorporated herein by reference). Matteucci et al. (1981) J. Am. Chem. Soc. 103:3185-3191, describes the use of phosphochloridites in the preparation of oligonucleotides. Beaucage et al. (1981) Tetrahedron Lett. 22:1859-1862, and U.S. Pat. No. 4,415,732 describe the use of phosphoramidites in the preparation of oligonucleotides. Smith (1983) ABL 15-24, the references cited therein and Warner et al. (1984) DNA 3:401-411 describe automated solid-phase oligodeoxyribonucleotide synthesis. U.S. Pat. Nos. 4,483,964 and 4,517,338 to Urdea et al. describe a method for synthesizing polynucleotides by selectively introducing reagents to a solid phase substrate in a tubular reaction zone. All of these references are herein incorporated by reference.

The present invention is not limited to any one synthesizer. Indeed, any type of synthesizer may be employed including, but not limited to, the synthesizers described above, MOSS EXPEDITE 16-channel DNA synthesizers (PE Biosystems, Foster City, Calif.), OligoPilot (Amersham Pharmacia,), 3948 48-Channel DNA synthesizers (PE Biosystems, Foster City, Calif.), and Northwest Engineering 48-Column Oligonucleotide Synthesizer (NEI-48, Northwest Engineering, Inc., Alameda, Calif.)

As mentioned above, preferably synthesis proceeds from a 3' end group attached to a solid support (which is preferably located in a synthesis column). The present invention is not limited by the type of solid support. A wide variety of supports can be used for solid phase synthesis of an oligonucleotide. Examples of suitable support materials include, but are not limited to, polysaccharides such as agarose, dextran, polyacrylamides, poly(dimethylacrylamide), poly(acrylmorpholide), polystyrenes, polystyrene grafted onto poly(tetrafluoroethylene), non-swellable polystyrene, polyvinyl alcohols, copolymers of hydroxyethyl methacrylate and methyl methacrylate, silicas, teflons, glasses, Porasil C, controlled pore glass ("CPG"), kieselguhr, cellulose, Fractosil 500, and the like, as described in U.S. Pat. No. 5,256,549 to Urdea et al., herein incorporated by reference.

In some embodiments, instead of the 3' end group being attached to the solid support, the 3' end group is attached to a linker, which in turn is attached to the solid support. In certain embodiments, this linker is selectively cleavable (e.g. such that cleavage of this linker can be used to release the 3' end tagged oligonucleotide from the solid support). In some embodiments, the 5' end of the oligonucleotides is also labeled (preferably with a moiety different from the 3' end group). Examples of linkers and 5' end labeling moieties and strategies are provided in U.S. Pat. No. 6,472,522 (herein incorporated by reference for all purposes).

In certain embodiments, once the 3' oligonucleotides are synthesized on the solid support, the solid support is exposed to reagents that cleave any abasic (e.g. apurinic sites) present in the oligonucleotides. In this regard, these abasic sites do not get cleaved later generating oligonucleotide fragments that are capable of generating background in nucleic acid detection assays, such as the INVADER assay. Methods for cleaving such abasic sites are described in Horn et al. (1988) in Nucleic Acids Res. 16:11559-11571, and in Kwiatkowski et al. (1996) Nucleic Acids Res. 24:4632-4638, both of which are explicitly incorporated herein by reference for all purposes.

In some embodiments, once the 3' end tagged oligonucleotides are synthesized, the oligonucleotides are purified based on affinity for the 3' end group. For example, the 3' end group can be used to purify the oligonucleotides (e.g. after being cleaved from a solid support) by column chromatography or cartridge purification or similar means. In preferred embodiments, the 3' end group is a lipophilic moiety. Oligonucleotides with 3' end lipohilic moieties may be purified by Water Oasis HLB columns or SUPERPURE columns, or similar devices.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); DS (dextran sulfate); C (degrees Centigrade); and Sigma (Sigma Chemical Co., St. Louis, Mo.).

EXAMPLE 1

Preparation of CPG Supports Modified with a Lipophilic Moiety

This example describes a method for producing CPG supports for oligonucleotide synthesis that are coupled to a linear organic aliphatic lipophilic moiety, specifically $C_{12}$, $C_{14}$, or $C_{16}$. The synthesis procedure involved three steps: (1) monoprotection of diol; (2) activation of the unprotected —OH; and (3) coupling to CPG.

A schematic representation of the synthesis procedure is shown below for $C_{14}$ (n=11) and $C_{16}$ (n=13). It is noted that in some embodiments (not shown in this Example) n is another number to generate other lipophilic moiety modified solid supports.

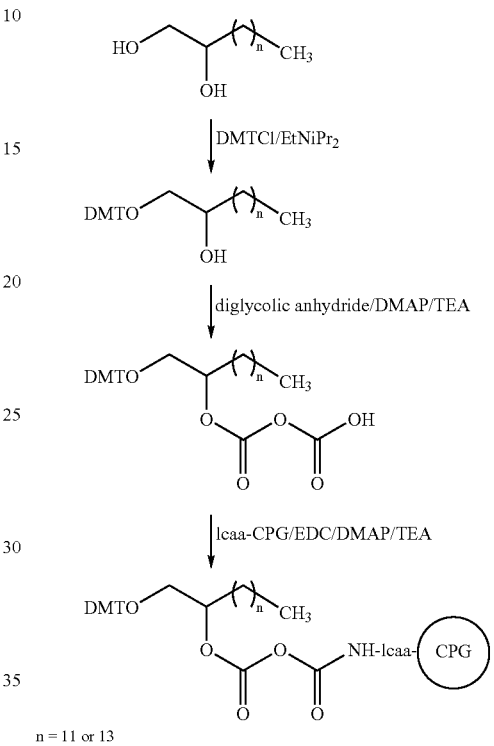

n = 11 or 13

The schematic representation of the synthesis procedure is shown below for $C_{12}$.

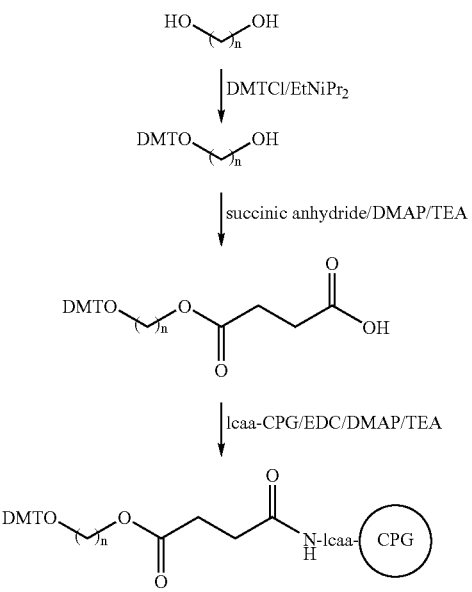

n = 12

1. Monoprotection of Diol

Table 1 lists the reagents used in each monoprotection reaction.

TABLE 1

| Compound | $C_{12}$ | $C_{14}$ | $C_{16}$ |
|---|---|---|---|
| 1,12-dodecanediol (MW 202.34) | 3 g (14.8 mmol) | — | — |
| 1,2-tetradecanediol (MW 230.39) | — | 2 g (8.7 mmol) | |
| 1,2 hexadecanediol (MW 258.45) | — | — | 2 g (7.7 mmol) |
| DMTC1 | 1.67 g (4.9 mmol) | 1.47 g (4.3 mmol) | 1.3 g (3.9 mmol) |
| N,N-diisopropylethylamine (Hunig's Base) | 633 mg (4.9 mmol) | 834 mg (6.45 mmol) | 750 mg (5.8 mmol) |
| Yield (%) | 0.74 g (30) | 2.18 g (94.8) | 1.82 g (83.1) |

Each diol was dissolved in 50 mls tetrahydrofuran. N,N-diisopropylethylamine was added with a syringe. The protectant DMT-C1 was added as a solid with stirring and was stirred overnight at room temperature under a drying tube. Reaction products were tested by TLC to confirm that the reaction was complete. Products were concentrated on a rotovap and purified on a silica column (70×230 mesh, 60 Å, 5.5×16 cm). A column was poured, loaded, and run with a 50/50 mixture of ethyl acetate/hexanes, 5% triethylamine (TEA). Fractions were collected, combined, and concentrated on the rotovap. Yields of each product are stated in Table 1 in terms of total quantity and percentage of theoretical maximum.

2. Activation of Unprotected-OH

Table 2 lists the reagents used in each activation reaction.

Each monoprotected diol was dissolved in $CH_2Cl_2$. TEA was added by syringe; succinic or diglycolic anhydride and DMAP were added as solids. The mixture was stirred at room temperature under a drying tube for 2 hours (overnight for $C_{12}$ product). Reaction products were tested by TLC to confirm that the reaction was complete and then concentrated on a rotovap and purified on a silica column (70×230 mesh, 60 Å, 4×17 cm). A column was poured, loaded, and run with 5% methanol, 5% TEA, $CH_2Cl_2$. Fractions were collected, combined, and concentrated on the rotovap. Yields of each product are stated in Table 2 in terms of total quantity and percentage of theoretical maximum.

3. Coupling to CPG

Table 3 lists the reagents used in the reactions to couple the activated succinate (for the $C_{12}$ product) or diglycolates to the CPG.

TABLE 2

| Compound | $C_{12}$ | $C_{14}$ | $C_{16}$ |
|---|---|---|---|
| $C_{12}$ deprotected product (MW 504.7) | 725 mg (1.43 mmol) | — | — |
| $C_{14}$ deprotected product (MW 532.8) | — | 800 mg (1.5 mmol) | — |
| $C_{16}$ deprotected product (MW 560.8) | — | — | 800 mg (1.43 mmol) |
| Succinic anhydride | 215 mg (2.15 mmol) | — | — |
| Diglycolic anhydride (90%) | — | 261 mg (2.25 mmol) | 250 mg (2.15 mmol) |
| DMAP | 88 mg (0.72 mmol) | 92 mg (0.75 mmol) | 87 mg (0.72 mmol) |
| TEA | 219 µl (1.57 mmol) | 230 µl (1.65 mmol) | 220 µl (1.57 mmol) |
| Yield g (%) | 0.69 g (68%) | 0.83 g (74) | 1.05 g (95) |

TABLE 3

| Compound | $C_{12}$ | $C_{14}$ | $C_{16}$ |
| --- | --- | --- | --- |
| Long chain alkyl amine (lcaa) CPG, 1000 Å, loading capacity 69 µmol/g (Glen Research, Sterling, Va) | 1 g | — | — |
| Long chain alkyl amine (lcaa) CPG, 906 Å, loading capacity, 141 µmol/g (AIC, Natick, MA) | — | 2 g | 2 g |
| Dodecane succinate (MW 704.95) | 56 mg (80 µmol) | — | — |
| Tetradecane glycolate (MW 749.05) initial aliquot/total | — | 60 mg/180 mg (240 µmol) | — |
| Hexadecane glycolate (MW 777.05) | — | — | 63 mg/183 mg (240 µmol) |
| DMAP | 1.9 mg (16 µmol) | 1.9 mg (16 µmol) | 1.9 mg (16 µmol) |
| EDC | 61 mg (320 µmol) | 61 mg/183 mg (960 µmol) | 61 mg/183 mg (960 µmol) |
| TEA | 9.7 mg (96 µmol) | 9.7 mg (96 µmol) | 9.7 mg (96 µmol) |
| Total loading (µmol/g CPG)/mg CPG/µmol | 69/15 | 20.5/49 | 20.5/49 |

An aliquot of the appropriate succinate or diglycolate dissolved in 15 mls of pyridine was added to 2 g of CPG. 1.9 mg DMAP and 61 mg of EDC were added as solids, and 9.7 mg of TEA in 13 mls was added by syringe. The mixture was vortexed at room temperature. For the $C_{14}$ and $C_{16}$ CPG syntheses, additional aliquots of 1-ethyl-(3-dimethylaminopropyl)carbodiimide hydrochloride and the appropriate diglycolate were added in two additional aliquots equal to the initial aliquot to the reaction slurry to achieve a final loading of at least 20 µmol/g CPG. The support was filtered, washed with acetonitrile, and dried with argon flow. The material was capped with an equal mixture of 6% 4-(dimethylamino) pyridine in acetonitrile and 2/3/5 (acetic anhydride/2,4,6-collidine/acetonitrile; 100 ml total volume) for 2 hours. The support was filtered, washed with pyridine, methanol, and methylene chloride, and dried overnight under vacuum. The loading was calculated by combining a known mass of CPG and known volume of 3% dichloroacetic acid/methylene chloride and measuring the absorbance of the solution at 504 nm to determine the concentration of the released trityl cation.

In all synthetic steps leading to the production of the solid supports, standard reaction conditions and coupling protocols were employed [See, e.g., (1) Letsinger, R. L. and Lunsdorf, W. B., J. Am. Chem. Soc. 98, 3655-3661 (1976); (2) Caruthers, M H., et al. Methods Enzymol. 154; 287-313 (1987); (3) Hovinen, J. et al. Tetrahedron Lett. 34, 5163-5166 (1993); (4) Montserat, F. X. et al. Nucleotides, Nucleosides 12, 967-971 (1993); (5) Guzaev, A., et al. Tetrahedron 50, 7203-721 (1994); (6) Pon. R. T. and Yu, S, Nucleic Acids Res. 25, 3629-3635 (1997), all of which are herein incorporated by reference]. The efficiency of the coupling reaction to the 1caa-CPG solid support was estimated by measuring the concentration of the DMT cation released from the support after treatment with 3% dichloroacetic acid in dichloromethane. The amount of the appropriate succinate or diglycolate conjugated to the CPG was calculated as indicated in Table 3.

EXAMPLE 2

Synthesis and Purification of Probe Oligonucleotides Containing $C_{12}$, $C_{14}$, or $C_{16}$ 3' End Groups This example describes synthesis and purification of oligonucleotides containing 3' end groups. In particular, this example describes synthesis of oligonucleotide using the $C_{12}$, $C_{14}$, or $C_{16}$ conjugated solid supports described above, as well as purification of the resulting 3' end tagged oligonucleotides.

To perform the synthesis, CPG containing 1 µmol of the attached succinate or diglycolate was loaded into cartridges compatible with the PerSeptive Biosystems Expedite automated DNA synthesizer. Oligonucleotides containing the $C_{12}$, $C_{14}$, or $C_{16}$ modifications were synthesized in 1 µmol scale on the PerSeptive Biosystems Expedite automated DNA synthesizer using the standard phosphoramidite coupling protocol with DMT off. Cleavage (off CPG) and deprotection was performed with ammonium hydroxide in a final volume of 500 µl overnight at 55° C.

The sequences that were synthesized were all specifically designed as probe oligonucleotides (downstream oligonucleotides) for use in an invasive cleavage assay (in this case the INVADER assay). The following six sequences were used, each oligonucleotide synthesized separately with the $C_{12}$, $C_{14}$ and $C_{16}$ lipophilic 3' end groups:

```
                                         (SEQ ID NO:1)
1. 5' CGCGCCGAGGACCTTTGGAAGCTTGTAT 3'

(SEQ ID NO:2)
2. 5' ACGGACGCGGAGGCCTTTGGAAGCTTGT 3'

(SEQ ID NO:3)
3. 5' CGCGCCGAGGATGACATGATTACTGAGAGTT 3'

(SEQ ID NO:4)
4. 5' ACGGACGCGGAGGTGACATGATTACTGAGAGT 3'

(SEQ ID NO:13)
5. 5' ACGGACGCGGAGGATTAGGGTTTGACTTATATGTG 3'

(SEQ ID NO:14)
6. 5' CGCGCCGAGGAATTAGGGTTTGACTTATATGTG 3'
```

The following two sequences were also employed, however, these sequences were only synthesized such that the 3' end of the resulting oligonucleotides contained a $C_{16}$ lipophilic 3' end group:

(SEQ ID NO:18)
7. 5' <u>CGCGCCGAGG</u>TGCTGTGTCCATGGA 3'

(SEQ ID NO:19)
8. 5' <u>ATGACGTGGCAGAC</u>CGCTGTGTCCATGG 3'

For each of these sequences, the 5' portion ("flap") is highlighted with underlining. The remaining non-underlined part of the sequences is the 3' portion (Target Specific Region). Also, fragments that would be generated during an invasive cleavage reaction with these sequences (and the indicated INVADER oligonucleotides shown in the following Examples) are the underlined sequence (5' portion) plus the first base (in bold) from the 3' portion. These fragments are designed to participate in a second invasive cleavage reaction with a FRET cassette by serving as the INVADER (upstream) oligonucleotide in this second invasive cleavage reaction.

Following synthesis and cleavage from the CPG supports, all oligonucleotide preparations were concentrated in concentrated $NH_4OH$ at 55° C. overnight, then filtered through 0.2 μm teflon syringe filter, dried in a speedvac, dissolved in 1 ml distilled $H_2O$, and spun briefly to pellet particulate contaminants. Two 50 μl aliquots of each oligonucleotide (approximately 50 nmol) solution were removed, dried in a speedvac, suspended in 50 μl distilled $H_2O$, and purified in parallel on either an affinity purification column (described below) or by reverse phase HPLC for comparison. HPLC analyses were performed with a Hitachi D-7000 Interface, L-7100 gradient pump, and L-7400 UV detector using a Varian Omnisphere 5 C18 column (250×4.6 mm) and 100 mM TEAA, pH 7/acetonitrile, gradient 4% acetonitrile/min.

Column Affinity Purification

In order to purify the 3' end tagged oligonucleotides based on the lipophilic moiety at the 3' end ($C_{12}$, $C_{14}$, or $C_{16}$), a column affinity purification method was employed. In particular, Waters OASIS HLB extraction cartridge cat #94225 (Milford, Mass) columns were employed. The Waters Oasis HLB columns were washed with 1 ml acetonitrile, followed by a wash with 1 ml of 100 mM TEAA prior to application of the oligonucleotide sample. Each 50 μl aliquot of oligonucleotide was added to 950 μl of 100 mg/ml NaCl/5% DMF, and the entire 1 ml solution was applied to the columns. The column to which the $C_{12}$-containing oligonucleotide was applied was washed with 1 ml of 5% acetonitrile/100 mM TEAA. All columns were washed with 1 ml of 10% acetonitrile/100 mM TEAA. Prior to elution, each column was washed with 2 mls of distilled $H_2O$. Oligonucleotides were eluted from the columns with 0.5 ml 50/50 acetonitrile and distilled $H_2O$, dried down, and submitted for INVADER assay analysis as described in Example 3.

EXAMPLE 3

Comparative Performance of HPLC-Purified, Non-Tagged Oligonucleotides Vs. Affinity-Purified, 3' Tagged Oligonucleotides in a Nucleic Acid Detection Assay This example describes a comparison between the two sets of oligonucleotides produced as described above (i.e. the HPLC-purified, non-tagged oligonucleotides, and the affinity purified, 3'-tagged oligonucleotides). In particular, this example compares the ability of these two sets of oligonucleotides to function in the INVADER detection assay. As the results below demonstrate, the inclusion of these lipophilic 3' end groups does not inhibit the INVADER reaction. These experiments further illustrate that 3' end affinity purification may be used to generate oligonucleotide compositions that function as well as oligonucleotide compositions purified by HPLC.

In this example, SEQ ID NOs:1-4 (labeled with $C_{12}$, $C_{14}$, or $C_{16}$ linkers as described above) were employed as probe oligonucleotides in the INVADER assays (as described below). SEQ ID NOs 1 and 2 are probe oligonucleotides specific for either allele of SNP rs4574 (dbSNP_ID), referred to herein as "D 26." SEQ ID NOs: 3 and 4 are probe oligonucleotides specific for either allele of SNP rs7799 (dbSNP_ID), referred to herein as "D 41."

INVADER assays were set up to detect wild type and variant versions of SNPs D26 and D41. Target DNA was provided as a PCR product using 5' GGAATGCCGTCTTG-GAAGCC 3' (SEQ ID NO:5) as a forward primer and 5' CCCGGCTTACCTTATAGACCACC (SEQ ID NO:6) as a reverse primer for D26 and 5' AACATGTTCCTGGTGCT-GATATTCTCA 3' (SEQ ID NO:7) as a forward primer and 5' CACCTGTAAGGGTGATGTCATCATCA 3' (SEQ ID NO:8) as a reverse primer for D41. PCR reactions were multiplexed to amplify 96 distinct regions. Reaction mixtures contained the following final concentrations in a volume of 50 μl:10 mM Tris, pH 7.5, 100 mM KCl, 3 mM $MgCl_2$, 200 μM each dNTP, 25 nM each primer, 2 μl of a mixture of TaqStart Antibody, Clonetech (Mountain View, Calif.), 1.1 g/μl, Cat no 5400-1 and AmpliTaq® DNA Polymerase (Applied BioSystems, Foster City, Calif.) 5U/μl, which was incubated at room temperature for 10 min prior to addition to the reaction. PCR products were diluted 1:50 prior to inclusion in the INVADER assay.

Biplex INVADER reactions (e.g. as shown in FIG. 1) were carried out in a final volume of 6 μl in a 384-well microplate containing the following reagents dried down directly in the microplate wells: 32 ng/reaction of the CLEAVASE XI enzyme (Third Wave Technologies, Madison, Wis.) and FRET oligonucleotides (fam) tct (Z28) agc cgg ttt tcc ggc tga gac ctc ggc gcg-hexanediol (SEQ ID NO:9) (FAM) and (red dye) tct (Z28) agc cgg ttt tcc ggc tga gac tcc gcg tcc gt-hexanediol (SEQ ID NO:10) (RED) at a final concentration of 0.25 μM each. A 3 μl volume containing the following reagents (all concentrations specified are final concentrations): primary probes (for D26 SEQ ID NO:1 and SEQ ID NO:2; for D41, SEQ ID NO:3 and SEQ ID NO:4), 0.5 M each; INVADER oligonucleotide (upstream oligonucleotide) [for D26, 5' CAGCGATGGTCGTGCC AGTTTTCCGGT 3' (SEQ ID NO:11); for D41, 5' CGGTCTAGCCTGTGTG-GAAG AGCCCAT 3' (SEQ ID NO:12)], 0.05 μM, 10 mM MOPS, and 15 mM $MgCl_2$.

Subsequently, 3 μl of diluted PCR product (target sequence) were added, and the reactions were covered with 6 μl mineral oil. For the no target controls, 3 μl of tRNA at a concentration of 10 ng/μl were added in lieu of target. Plates were sealed and incubated at 95° C. for 5 minutes to denature the target, then cooled to the reaction temperature of 63° C. Fluorescence signal was read after 15 and 30 minutes in a CytoFluor® 4000 fluorescence plate reader (Applied Biosystems, Foster City, Calif.). The settings used were: 485/20 nm excitation/bandwidth and 530/25 nm emission/bandwidth for F dye detection, and 560/20 nm excitation/bandwidth and 620/40 nm emission/bandwidth for R dye detection. The instrument gain was set for each dye so that the No Target Blank produced between 100-200 Absolute Fluorescence Units (AFUs).

The raw data that is generated by the device/instrument is used to measure the assay performance (real-time or endpoint mode). The equations below provide how FOZ, and other values are calculated. NTC in the equations below represents the signal from the No Target Control. Also, FOZ is an abbreviation for fold over zero. Net FOZ is calculated by subtracting 1 from FOZ to eliminate contribution from background signal.

FOZ or Signal/No Target $FOZ_{Dye1}=(RawSignal_{Dye1}/NTC_{Dye1})$.

$FOZ_{Dye2}=(RawSignal_{Dye2}/NTC_{Dye2})$.

The two FOZ values (i.e. wild type and mutant) for each sample were used to calculate the WT:Mut Ratio as follows:

$$Ratio = \frac{(Net\ WT\ FOZ)}{(Net\ Mut\ FOZ)}$$

where Net FOZ=FOZ−1

In the case of replicated runs, $RawSignal_{DyeX}$ and $NTC_{DyeX}$ are the averaged values.

Figure 2:
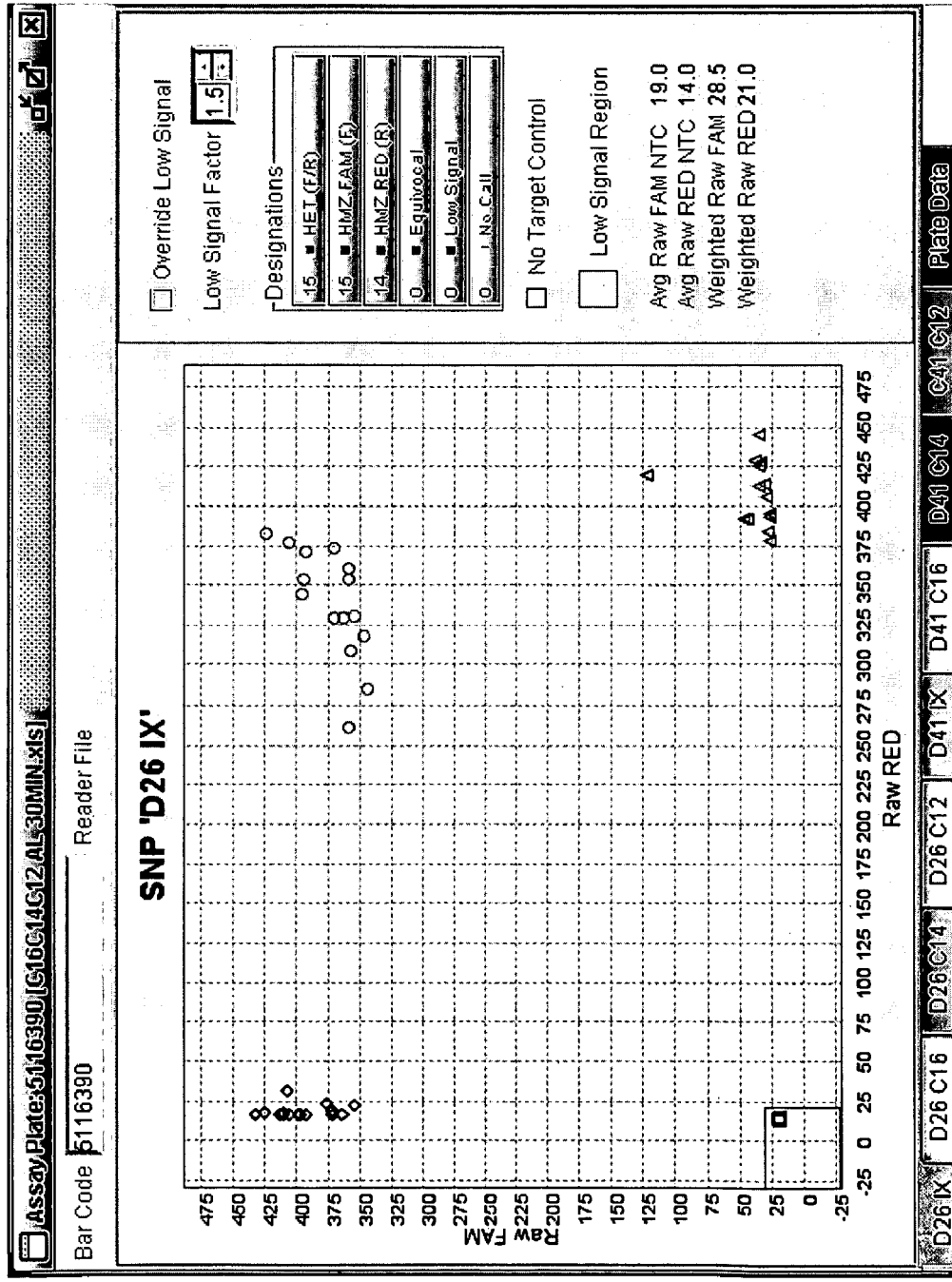
FIG. 2 shows the raw signal generated after 30 minutes by an INVADER assay designed to detect the D26 SNP using various probe oligonucleotides, including HLPC purified IX probe oligonucleotides, and affinity purified probe oligonucleotides with C16, C14, and C12 3' end groups.
Figure 2:
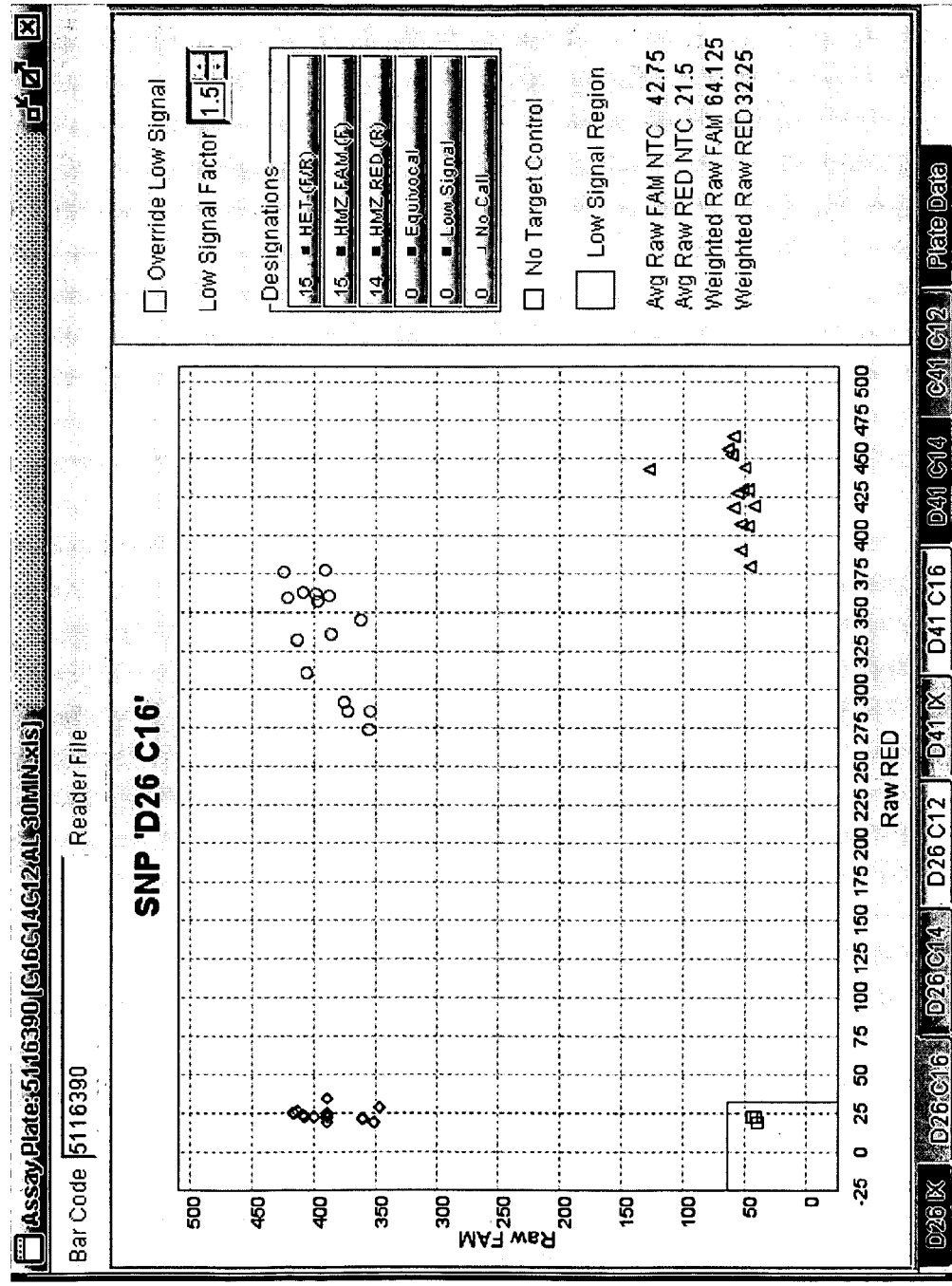
Figure 2:
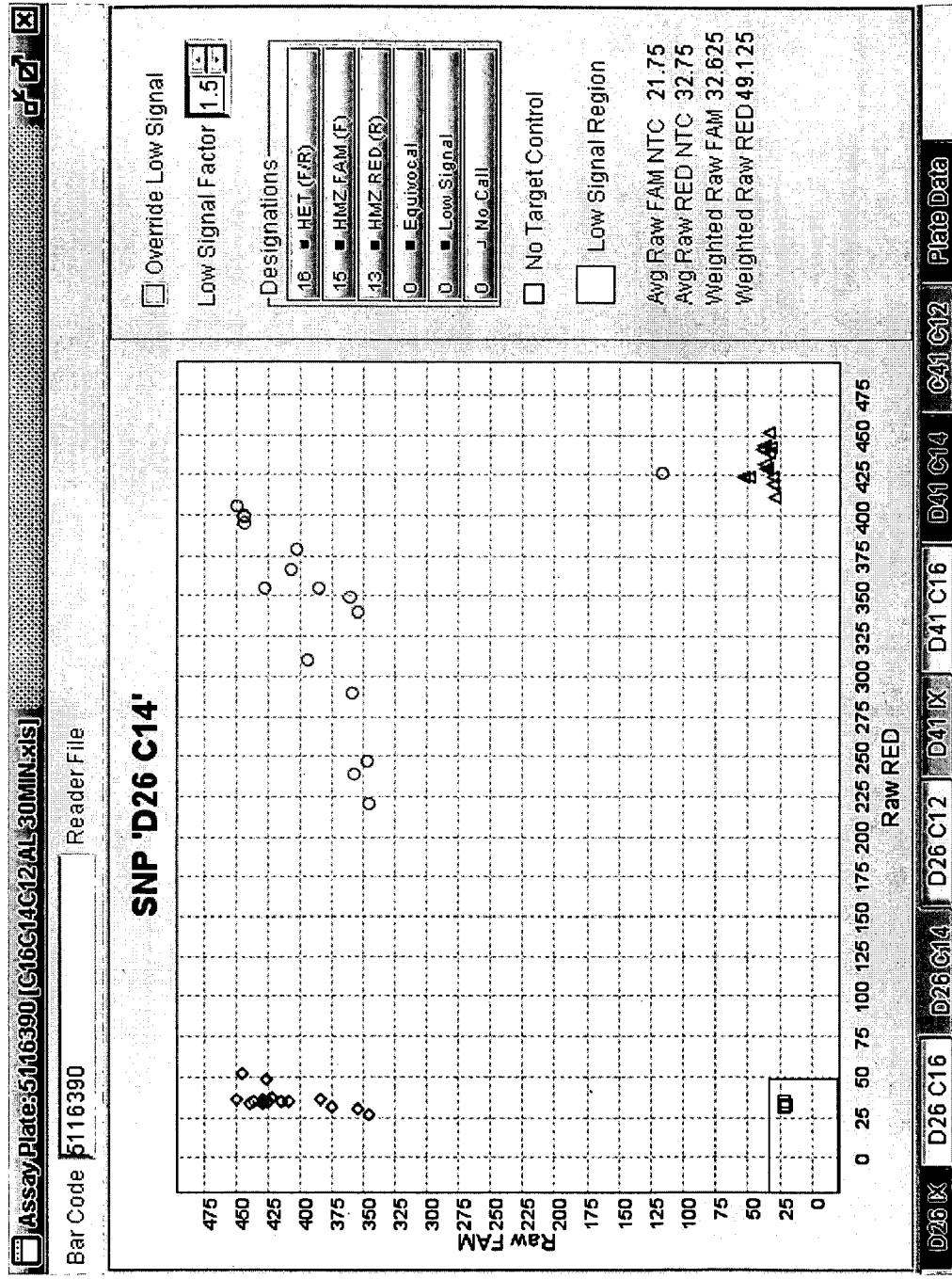
Figure 2:
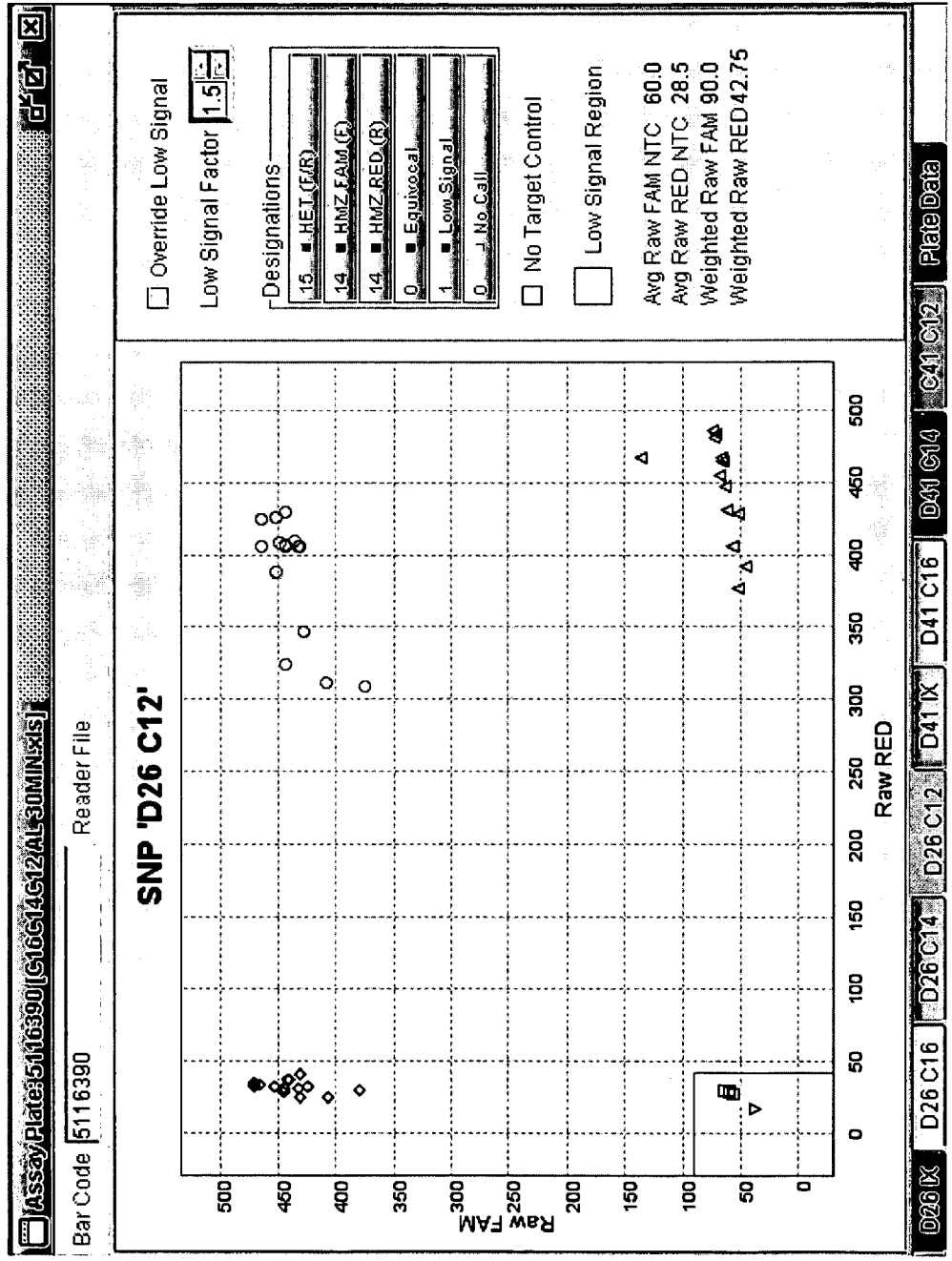

FIG. 2 shows the results of experiments designed to detect the D26 SNP. Raw RED counts are plotted on the X-axis; raw FAM, on the Y-axis. Data points clustered along the Y-axis are homozygous for the T, or wild-type allele, points clustered along the X-axis are homozygous for the C, or variant allele, and those clustered between the two axes are heterozygous. The box near the origin delimits an area of low signal defined as 1.5× the average obtained from the no target controls; data points lying within this box are not assigned a genotype. FIG. 2A shows the raw counts obtained after a 30-minute incubation using probe oligonucleotides containing a 3' hexanediol modification, purified by conventional HPLC using an ion exchange (IX) column. FIGS. 2B, 2C, and 2D show the results obtained after a 30-minute incubation using probe oligonucleotides containing a $C_{16}$, $C_{14}$, and $C_{12}$ linker, respectively and purified by the method described in Example 2.

Comparison of the raw signal generated in the INVADER assay indicates that all four purified probe oligonucleotides resulted in comparable signal and genotype differentiation.

Figure 3:
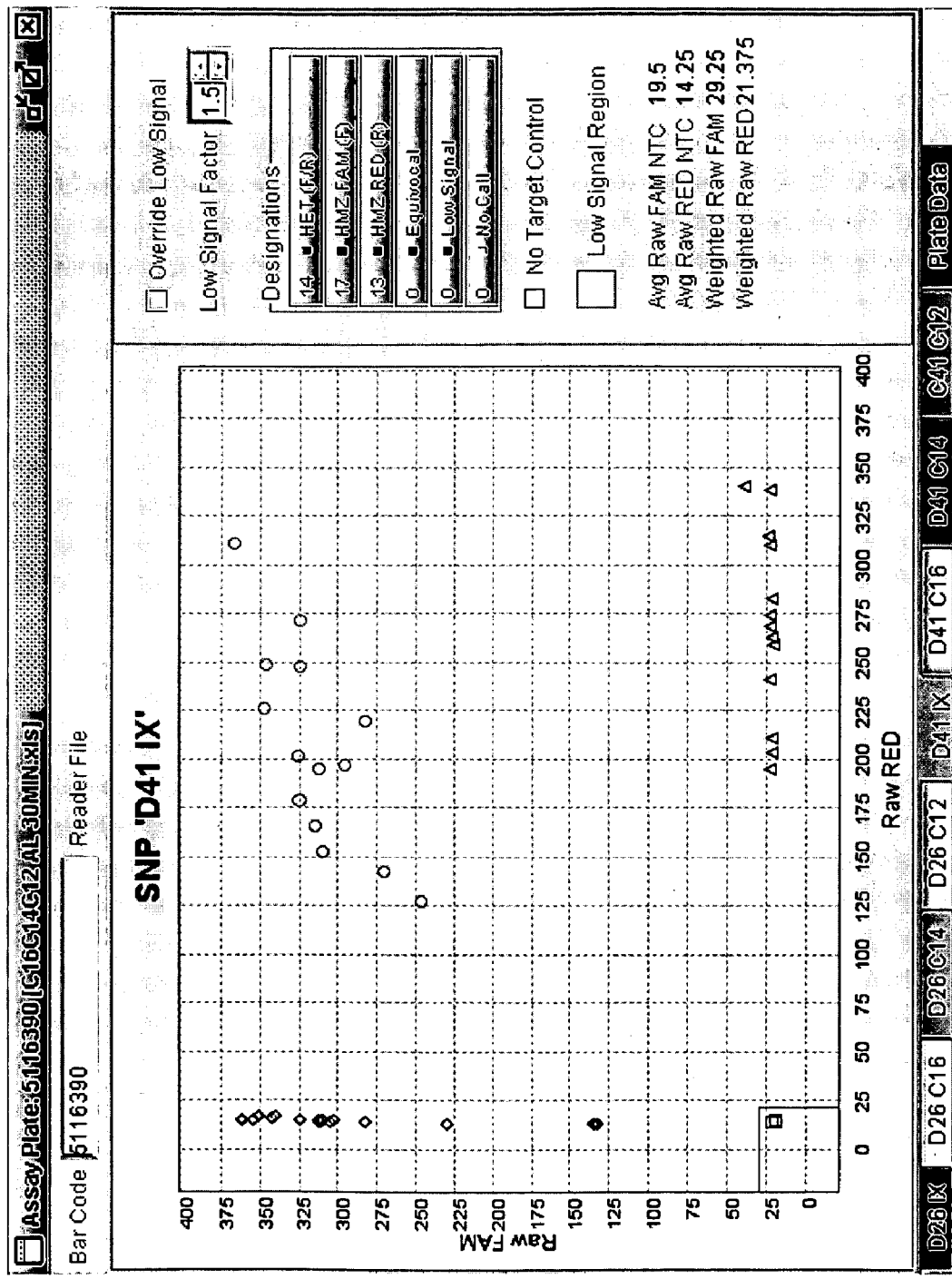
FIG. 3 shows the raw signal generated after 30 minutes by an INVADER assay designed to detect the D41 SNP using various probe oligonucleotides, including HPLC ion-exchange ("IX") purified probe oligonucleotides, and affinity purified probe oligonucleotides with $C_{16}$, $C_{14}$, and $C_{12}$ 3' end groups.
Figure 3:
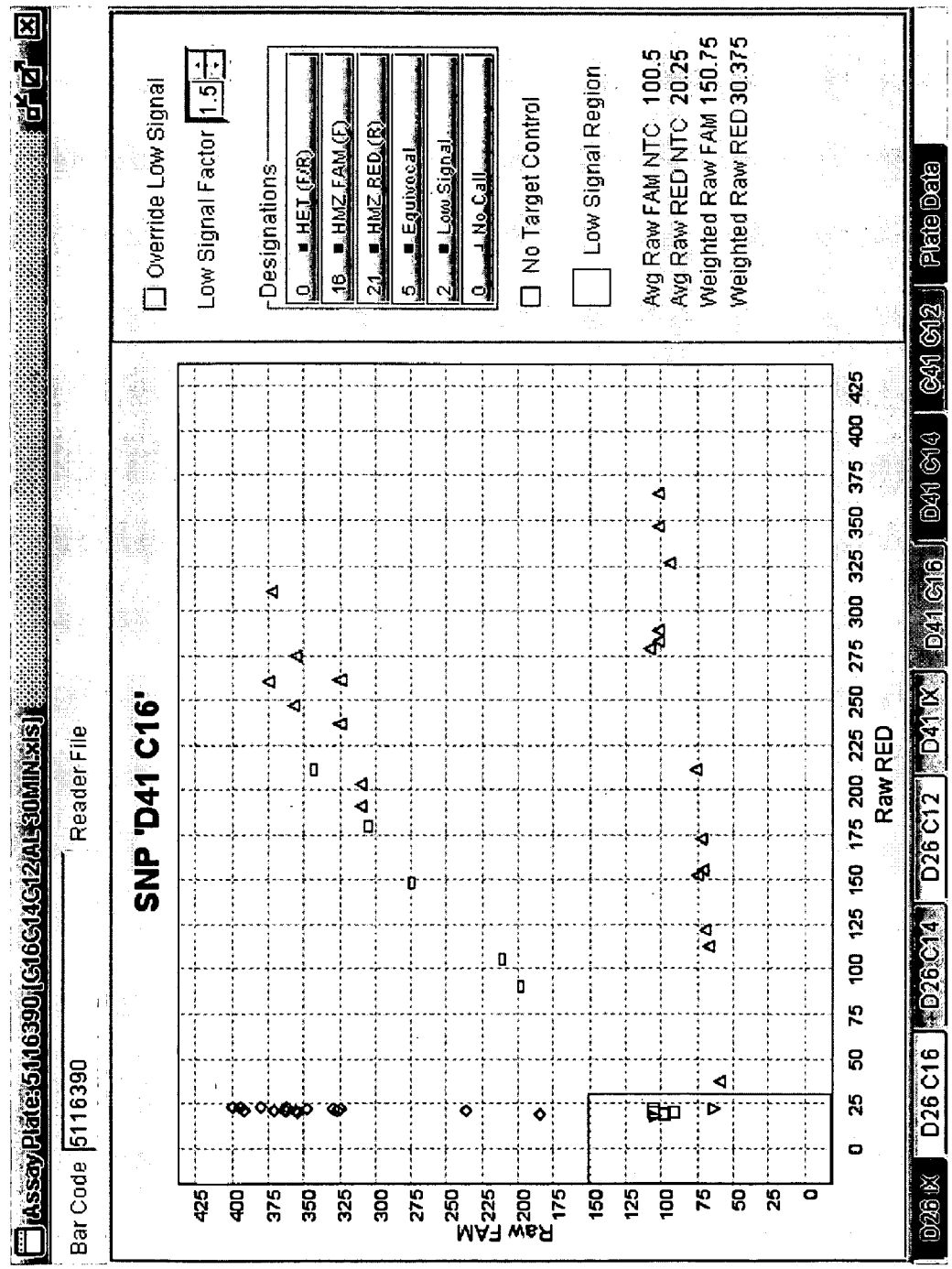
Figure 3:
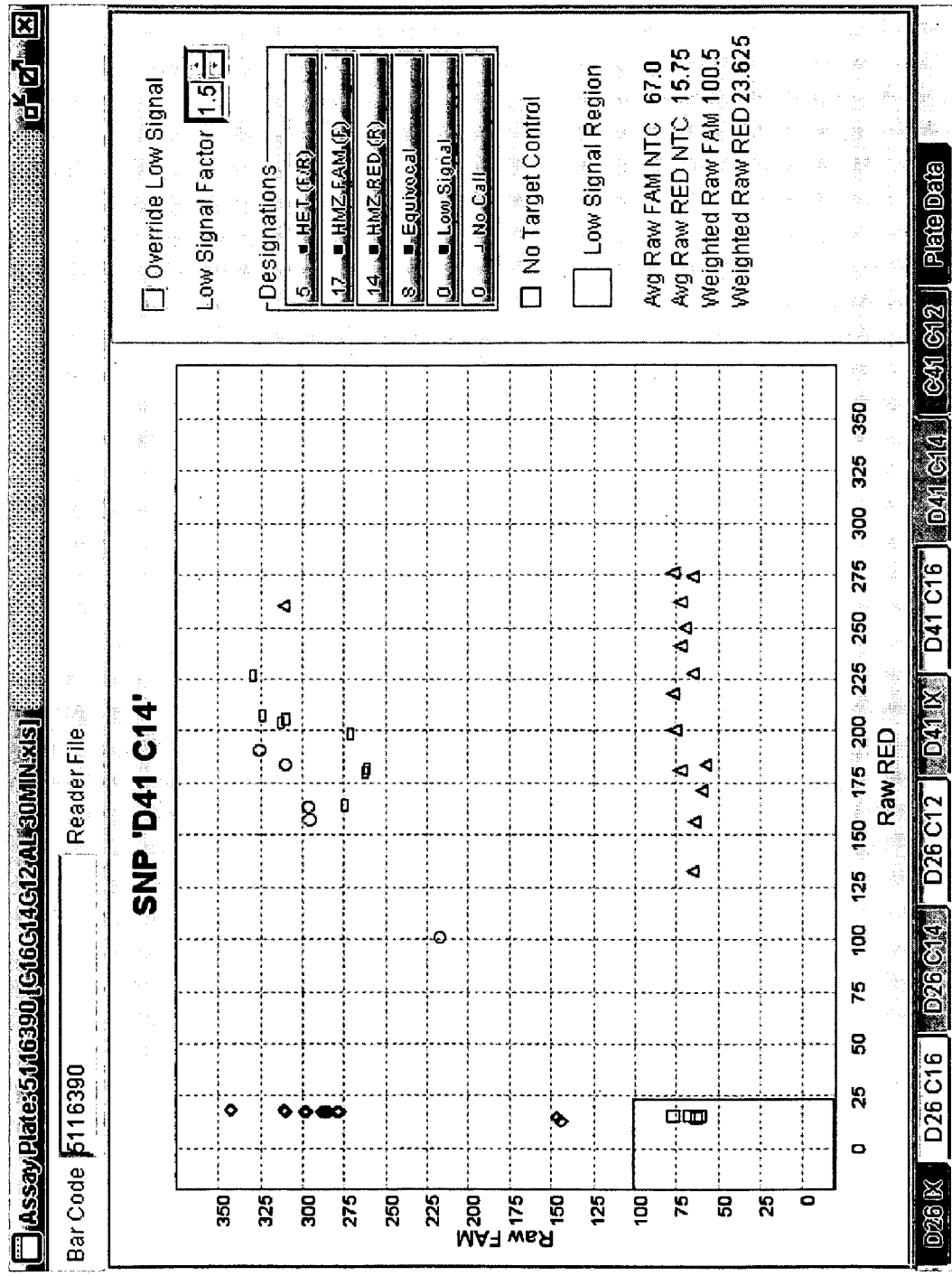
Figure 3:
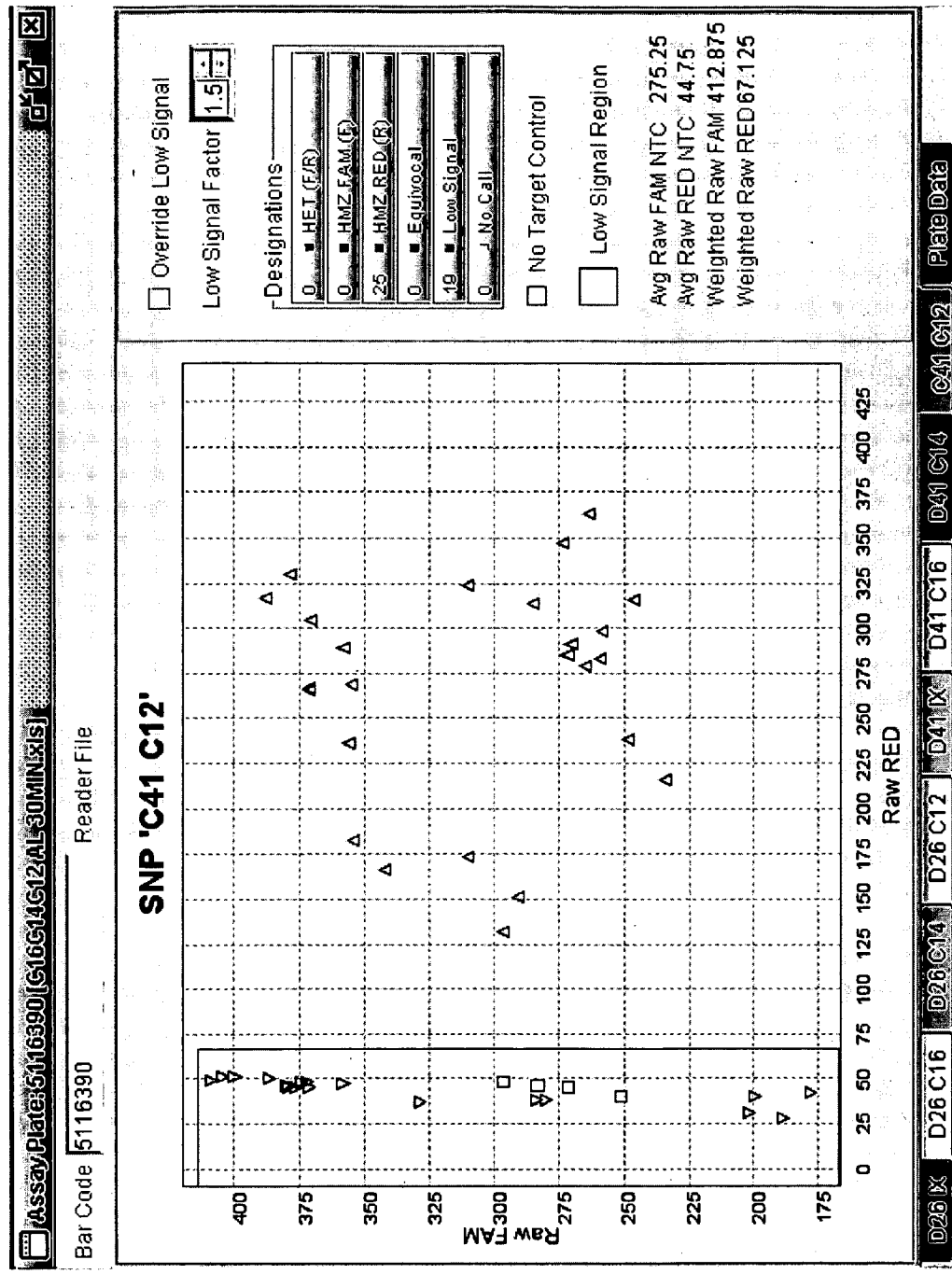

FIG. 3 shows the results of experiments designed to detect the D41 SNP. The data are plotted as described for FIG. 2. FIG. 3A shows the raw counts obtained after a 30-minute incubation using probe oligonucleotides containing a 3' hexanediol modification purified by conventional HPLC using an ion exchange (IX) column. FIGS. 3B, 3C, and 3D show the results obtained using primer oligonucleotides containing a $C_{16}$, $C_{14}$, and $C_{12}$ linker, respectively and purified by the method described in Example 2.

Comparison of the raw signal generated in the INVADER assay indicates that the probe oligonucleotides containing the $C_{14}$ and $C_{16}$ linkers yield results indistinguishable from those generated with the IX probe oligonucleotide. However, the purified probe oligonucleotide containing the $C_{12}$ linker failed to yield valid genotyping results for the homozygous allele detected with the FAM FRET cassette.

Figure 4:
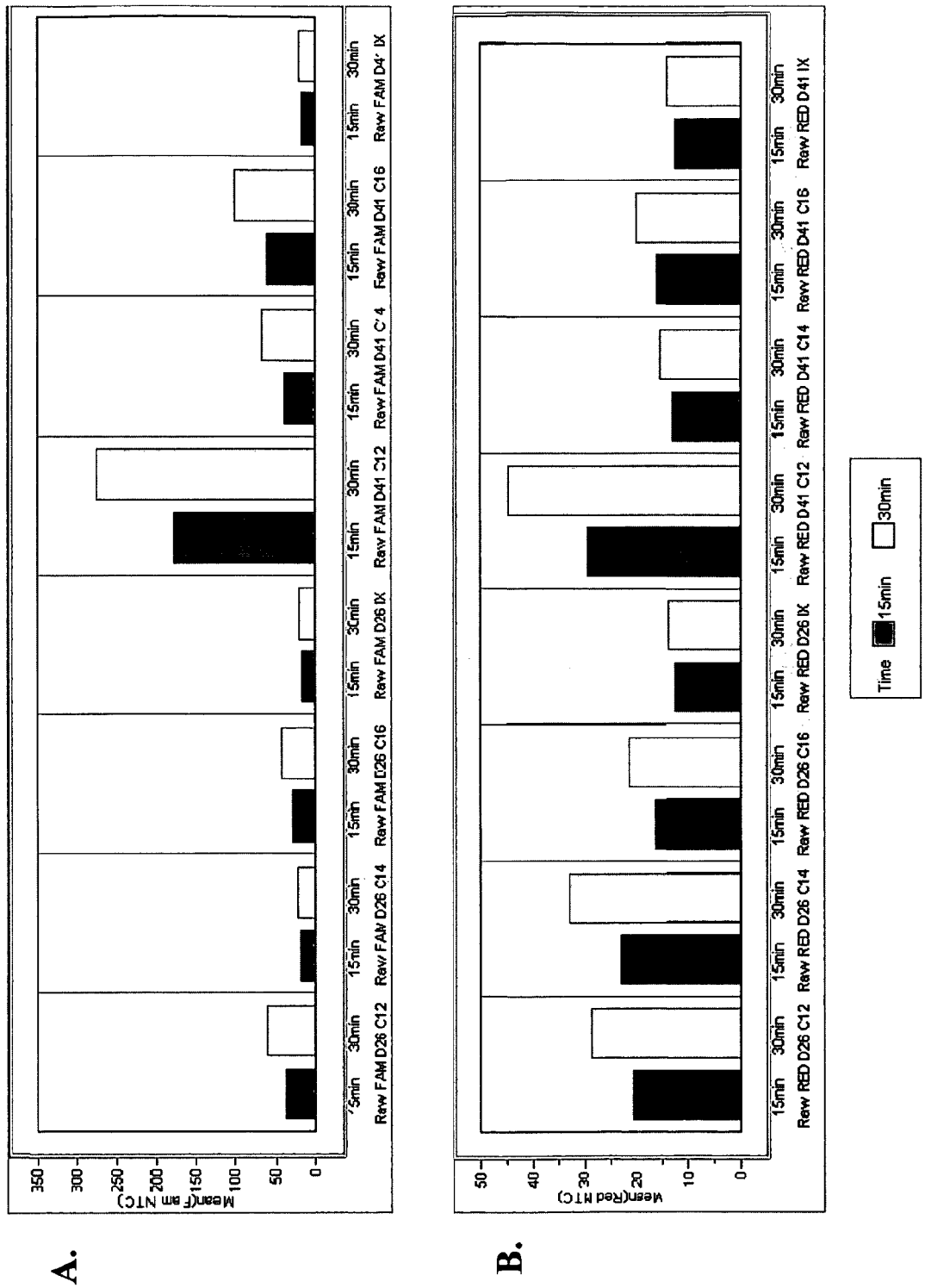
FIG. 4 shows the mean raw counts after 15 and 30-minute incubations of the no target controls (NTC) tested in the experiments presented in FIGS. 2 and 3.

FIG. 4 presents the mean raw counts after 15 and 30-minute incubations of the no target controls (NTC) tested in the experiments presented in FIGS. 2 and 3. With the exception of the $C_{12}$ probe oligonucleotide to detect D 41, all mean NTC levels were comparable for the $C_{12}$, $C_{14}$, $C_{16}$, and IX purified oligonucleotide probes. For the case of the D41 $C_{12}$ probe oligonucleotide, the mean NTC for both FAM and RED were above those obtained with all other probe oligonucleotides. The FAM NTC in particular was more than 4× higher than that obtained with any other probe. In this case, the high background obtained with the $C_{12}$ probe interfered with the ability of the INVADER assay to distinguish homozygotes reporting to FAM dye from the NTC samples.

EXAMPLE 4

Comparison of Unpurified $C_{16}$-Containing Oligonucleotides Vs. Those Purified by Ion-Exchange HPLC Chromatography or Oligonucleotide Purification Cartridge In this example, unpurified oligonucleotides for use as probe oligonucleotides in an INVADER assay containing $C_{16}$ linkers were compared in the INVADER assay to probe oligonucleotides containing a 3' hexanediol modification purified using ion exchange HPLC or oligonucleotides with a 3' end $C_{16}$ group purified by a purification cartridge. As the results presented below demonstrate, purification based on lipophilic interactions between the $C_{16}$ moiety and the oligonucleotide purification cartridge is as effective as ion-exchange HPLC in eliminating background signal found in unpurified, or crude, oligonucleotide preparations. These experiments further demonstrate that unpurified probe oligonucleotides are not suitable for use in the INVADER assay due to generation of high non-specific background signal.

Probe oligonucleotides SEQ ID NO:13 (wild-type) and SEQ ID NO:14 (variant) containing a $C_{16}$ moiety, synthesized and purified as described in Examples 1 and 2, were designed to detect two alleles of SNP rs2230061 (dbSNP_ID, based on cDNA), referred to herein as "D2". Target DNA was provided as a PCR product using 5' GGTTCCCT GAGAGTTC-CCAGCC 3' (SEQ ID NO:15) as a forward primer and 5' CAGAGGCT TGGGATGGTAATACTCAC 3' (SEQ ID NO:16) as a reverse primer. PCR reactions were multiplexed to amplify 96 distinct regions. Reaction mixtures contained the following final concentrations in a volume of 50 μl: 10 mM Tris, pH 7.5, 100 mM KCl, 3 mM $MgCl_2$, 200 μM each dNTP, 25 nM each primer, 2 μl of a mixture of TaqStart Antibody, Clonetech (Mountain View, Calif.), 1.1 μg/l, Cat no 5400-1 and AmpliTaq® DNA Polymerase, 5U/μl, Cat# N808-0160 which was incubated at room temperature for 10 min prior to addition to the reaction. PCR products were diluted 1:50 prior to inclusion in the INVADER assay.

Biplex INVADER assay reactions (e.g. as shown in FIG. 1) were carried out in a final volume of 6 μl in a 384-well microplate containing the following reagents dried down directly in the microplate wells: 32 ng/reaction of the CLEAVASE XI enzyme and FRET oligonucleotides SEQ ID NO:7 (FAM) and SEQ ID NO:8 (RED) at a final concentration of 0.25 μM each. A 3 μl volume containing the following reagents (all concentrations specified are final concentrations): primary probes (SEQ ID NO:13 and SEQ ID NO:14), 0.5 μM each; INVADER oligonucleotide 5' CCTTTCTCTCTCCAGTCCACAGAATCAGGCA ATATCCT 3' (SEQ ID NO:17), 0.05 μM, 10 mM MOPS, and 15 mM $MgCl_2$.

Subsequently, 3 μl of diluted PCR product (target sequence) were added, and reactions were covered with 6 μl mineral oil. For the no target controls (NTCs), 3 μl of tRNA at a concentration of 10 ng/μl were added in lieu of target. Plates were sealed and incubated at 95° C. for 5 minutes to denature the target, then cooled to the reaction temperature of 63° C. Fluorescence signal was read after 15 minutes in a CytoFluor® 4000 fluorescence plate reader (Applied Biosystems, Foster City, Calif.). The settings used were: 485/20 nm excitation/bandwidth and 530/25 nm emission/bandwidth for F dye detection, and 560/20 nm excitation/bandwidth and 620/40 nm emission/bandwidth for R dye detection. The instrument gain was set for each dye so that the No Target Blank produced between 100-200 Absolute Fluorescence Units (AFUs).

Figure 5:
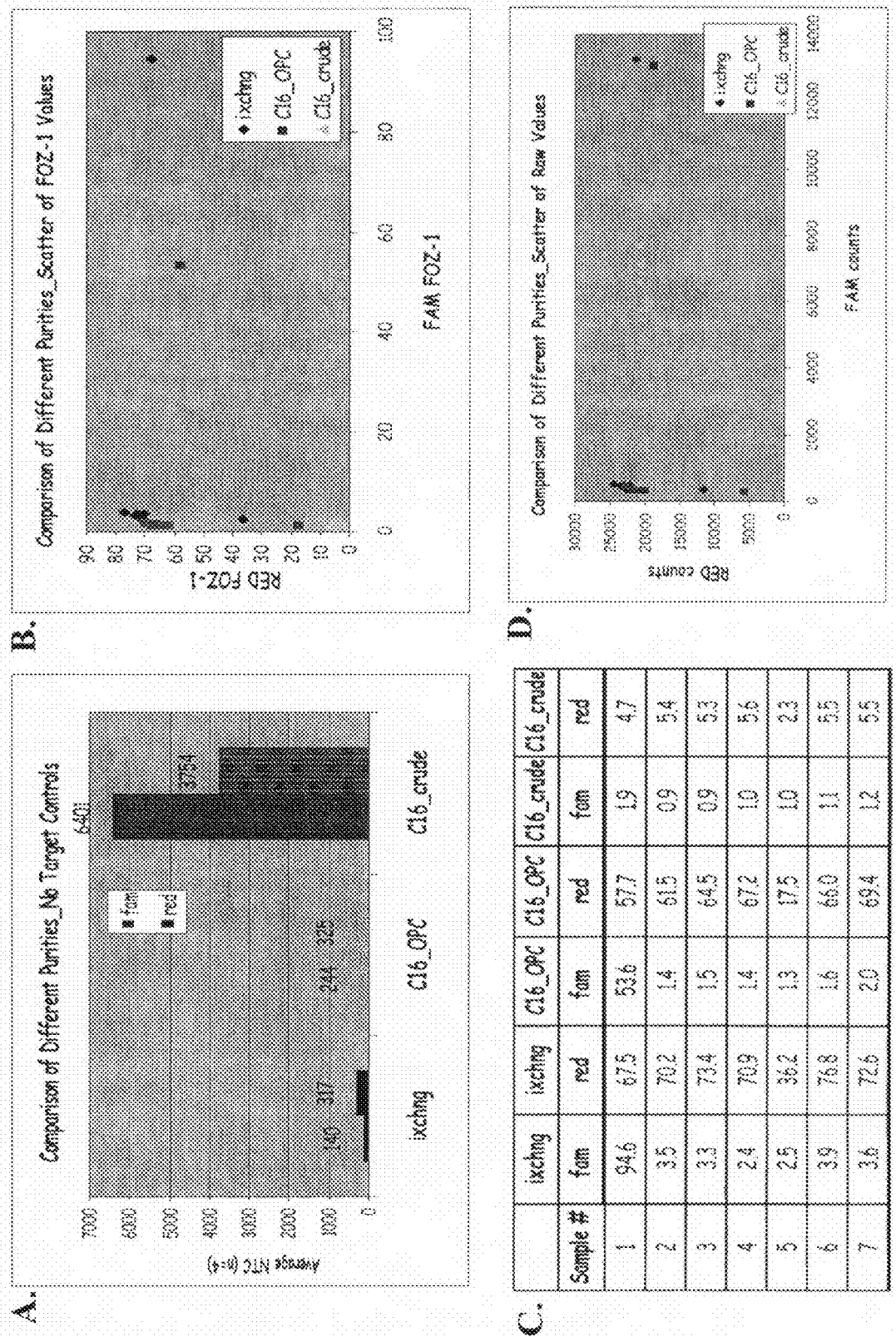
FIG. 5 shows the results of various assays (from Example 4) with three different probe oligonucleotides: IX (HPLC purified probes), C16 3' end tagged, cartridge purified probes, and C16 3' end labeled probes, un-purified.

FIG. 5 shows the results of experiments designed to detect the D2 SNP. The "ixchng" oligonucleotides contain a 3' terminal hexanediol to serve as a blocker that was added to these oligonucleotides during synthesis. The "C16_OPC" oligonucleotides contain a C16 linker synthesized as described in Example 1 and purified on a Waters OASIS HLB column as described in Example 2, and the "C16_crude" oligonucleotides were synthesized as described in Examples 1 and 2 but were not purified following removal from the CPG following synthesis.

FIG. 5A shows the results of the no target controls run with each of the two probes (SEQ ID NOs: 13 and 14) purified by either ion exchange HPLC ("ixchng"), lipophilic interactions on an oligonucleotide purification cartridge ("C16_OPC"), or not purified following synthesis ("C16_crude"). These results indicate that purification by ion-exchange HPLC and lipophilic interactions on an oligonucleotide purification cartridge yield comparable levels of background signal in the absence of target nucleic acid. However, the unpurified probe oligonucleotides generate significant levels of background signal.

FIGS. 5B-D present results obtained from use of these probe oligonucleotides in INVADER assays to detect both alleles of the D2 SNP. The data are plotted both as net fold-over-zero values (FIG. 5B) and as raw counts (FIG. 5D). The net-fold-over-zero values plotted in FIG. 5B provide an indication of signal above any background generated by the probe oligonucleotides in the absence of target. FIG. 5C includes a tabular representation of these data. An analysis of these data indicate that INVADER reactions carried out with both the HPLC-purified probes lacking a $C_{16}$ moiety (named "ixchng") and oligonucleotide purification cartridge-purified probe oligonucleotides with 3' end C16 groups (named "C16_OPC") generated valid and comparable results, but that INVADER results generated using unpurified probe oligonucleotides containing the $C_{16}$ moiety did not yield valid genotype calls. The unpurified, "crude" preparation of probe oligonucleotides failed to generate significant signal above background (likely due to the fact that the FRET probes are used up in the generation of non-specific background).

FIG. 5D shows these same data plotted as raw values and indicates that the unpurified oligonucleotides cause misrepresentation of the genotypes of the samples in this experiment. In particular, the data points generated with the crude probe oligonucleotide preparations appear to represent heterozygous samples. This misrepresentation is due to the high levels of both the FAM and RED target-independent signals generated by the unpurified probes. This presentation of the data further underscores the similarity of the oligonucleotide purification cartridge and ion exchange HPLC purified oligonucleotides.

EXAMPLE 5

Purification of $C_{16}$-Containing Oligonucleotides on SUPERPURE PLUS and TOP Cartridges This example describes a procedure for purifying oligonucleotides with 3' end groups (C16 in this example) using a SUPERPURE PLUS cartridge (Biosearch, Novato, Calif.) as well as TOP cartridges (Varian, Inc. Palo Alto, Calif.). In particular, this example describes procedures for SUPERPURE PLUS and TOP cartridge purification of a 200 mmol synthesis of 3'-$C_{16}$ probe (SEQ ID NOs: 18 and 19) cleaved and deprotected in 500 ul $NH_4OH$.

SUPERPURE PLUS Cartridge Purification
1) Wash cartridge with 3×0.5 ml acetonitrile
2) Wash with 3×0.5 ml 100 mM TEAA, pH 7
3) Apply Sample (200 nmol in 500 μl $NH_4OH$ c/d solution+ 0.5 ml 100 mg/ml NaCl/5% DMF)
4) Wash with 3×0.5 ml 15% ACN/100 mM TEAA
5) Wash with 4×0.5 ml water
6) Elute with 0.5 ml 25% acetonitile/65% water+1% Tween-20 OR
0.5 ml 10% Tween-20/water.

Elution with either procedure produces an oligonucleotide ready for use following quantification.

Probe oligonucleotides with SEQ ID NOs: 18 and 19 containing $C_{16}$ moieties synthesized as described in Examples 1 and 2 were purified by the above method and used in INVADER assays to detect SNP dbSNP_ID rs3813201, referred to herein as SNP "731" in synthetic targets as well as PCR products.

INVADER reactions on synthetic targets (5' CGGTTC-CATGGACAC AGCAGGGCTTTCTTGGACCTGTGAC-CTTAAGCCCA 3' [SEQ ID NO: 20] and 5' CGGTTCCATG-GACACAGCGGGGCTTTCTTGGACCTGTGACCTTAA GCCCA 3' [SEQ ID NO:21]) were set up in a 384-well microtiter plate containing 60 ng of CLEAVASE VII, a RED FRET cassette (5' (red dye) tct (Z28) tcg gcc ttt tgg ccg aga gac ctc ggc gcg (hexanediol)-3'[SEQ ID NO:22]), and a FAM FRET cassette (5' (fam) tct (Z28) agc cgg ttt tcc ggc tga gag tct gcc acg tca t (hexanediol) [SEQ ID NO: 23]), each at a final concentration of 0.25 μM. 3 μl of a master mix of primary probes (SEQ ID NOs: 18 and 19), INVADER oligonucleotide (5' GGCTTAAGGTCACAGGTCCAAGA AAGCCCA3' [SEQ ID NO:24]), MOPS, and $MgCl_2$, was added so that each reaction contained the following (final concentrations): 10 mM MOPS, pH 7.5, 7.5 mM $MgCl_2$, 0.5 μM each primary probe, and 0.05 μM INVADER oligonucleotide.

Figure 6:
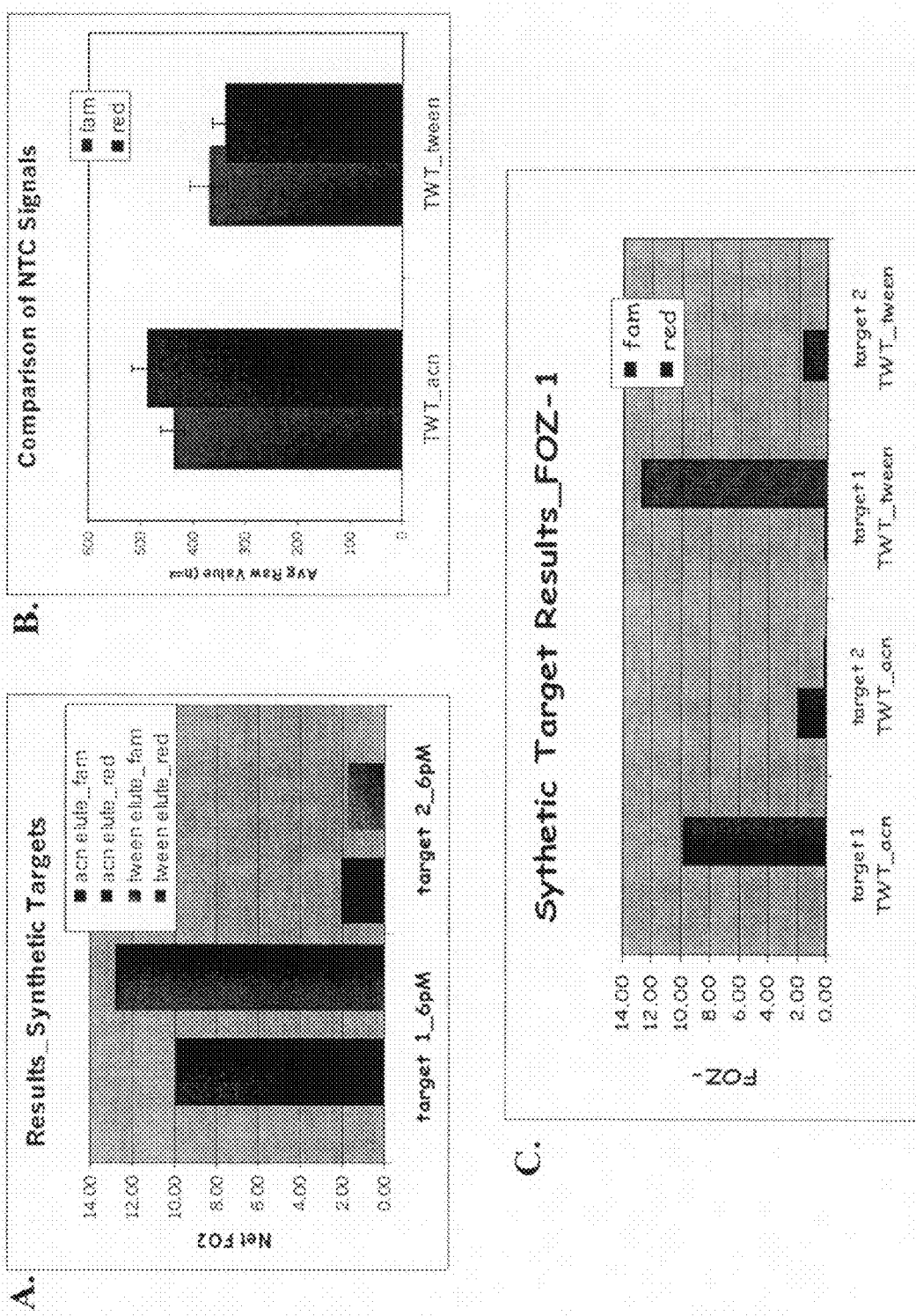
FIG. 6 shows the results of various assays (from Example 5) with $C_{16}$ 3' end tagged probe oligonucleotides purified by cartridge purification.

For the test samples, 3 μl of synthetic targets (SEQ ID NOs:20 and 21) were added to the appropriate wells to attain a final concentration of 3 pM. For the no target controls, 3 μl of tRNA at a concentration of 10 ng/μl were added in lieu of target. The reactions were covered with 6 μl of mineral oil and incubated at 95° C. for 5 minutes then cooled to 63° C. Fluorescence signal was read after 10 minutes of incubation at 63° C. FIG. 6A presents the INVADER assay results obtained from each target and indicates that either purification procedure (eluting with acetonitrile or Tween-20) results in probe oligonucleotides that function in the INVADER assay. FIG. 6B compares the average signal obtained from four no target control, or background, samples with each of the two probe oligonucleotides purified as described in this example.

FIG. 6C presents the results compiled from an analysis of SNP 731 in 40 patient samples. The samples were amplified in multiplex PCR reactions using 5' TGC AGGCTGCCTTA-CAGACC 3' (SEQ ID NO:25) as a forward primer and 5' CTGCTTGA AGCTGCCCAGGAA 3' (SEQ ID NO:26) as a reverse primer. PCR conditions were as described in Example 3. 3 μl of a 1:15 dilution of PCR products were used as targets in INVADER assays. INVADER assays were carried out as described in Example 3. These data demonstrate that oligonucleotides with 3' end $C_{16}$ groups can be effectively purified by cartridge chromatograpy. This example also demonstrates that the two methods of purifying probe oligonucleotides on the SUPERPURE PLUS cartridges yield identical genotyping calls and comparable signal generation as measured by fold-over-zero (FOZ).

TOP Cartridge Purification

A matrix of loading and elution conditions was applied to the analysis of purification using the either the 50 mg scale or 100 mg scale TOP cartridges as follows.

| | Load Method | | | |
|---|---|---|---|---|
| | 50% NH$_4$OH | 50% NH$_4$OH | 25% NH$_4$OH | 25% NH$_4$OH |
| | Elute Method | | | |
| | 50% ACN/1% Tween-20 | 10% Tween-20 | 50% ACN/1% Tween-20 | 10% Tween-20 |
| TOP column | 50 mg  100 mg | 50 mg  100 mg | 50 mg  100 mg | 50 mg  100 mg |

The load methods were as follows:
50% NH$_4$OH=500 μl NH$_4$OH cleave and deprotect solution+ 500 μl loading buffer
25% NH$_4$OH=500 μl NH$_4$OH cleave and deprotect solution+ 1.5 ml loading buffer The elute methods were as follows:
50% ACN/1% Tween-20=500 μl of a solution of 50% ACN and 49% water+1% Tween-20
10% Tween-20=500 μl of a solution of 10% Tween-20 in water.
Samples to be eluted with 50% ACN/1% Tween-20 were dried down following synthesis.
Samples to be eluted with 10% Tween-20 were not dried down following synthesis.
After loading, all columns were washed with 1 ml 15% ACN TEAA followed by 1 ml of dH$_2$O prior to elution as indicated.
Table 4 contains the % recovery obtained from each purification procedure.

TABLE 4

| | Load Method | | | | | | | |
|---|---|---|---|---|---|---|---|---|
| | 50% NH$_4$OH | | 50% NH$_4$OH | | 25% NH$_4$OH | | 25% NH$_4$OH | |
| | Elute Method | | | | | | | |
| | 50% ACN/1% Tween-20 | | 10% Tween-20 | | 50% ACN/1% Tween-20 | | 10% Tween-20 | |
| | TOP column | | | | | | | |
| | 50 mg | 100 mg | 50 mg | 100 mg | 50 mg | 100 mg | 50 mg | 100 mg |
| SEQ ID NO: 18 Yield nmoles | 73 | 72 | 33 | 44 | 52 | 74 | 42 | 32 |
| SEQ ID NO: 18 % recovery | 37 | 36 | 17 | 22 | 26 | 37 | 21 | 16 |
| SEQ ID NO: 19 Yield nmoles | 55 | 50 | 28 | 22 | 24 | 56 | 22 | 25 |
| SEQ ID NO: 19 % recovery | 28 | 25 | 14 | 11 | 12 | 28 | 11 | 13 |

All purified oligonucleotide preparations were used in Invader assays as described in this example. The purification procedure using TOP columns that worked best in conjunction with background generation and ability to differentiate genotypes was the 25% NH$_4$OH load with the 10% Tween-20 elution.

EXAMPLE 6

Detection of SNPs in Genomic DNA using C$_{16}$-Containing Probe Oligonucleotides on SUPERPURE PLUS Cartridges This example describes the use of Probe oligonucleotides containing a 3' C$_{16}$ moiety and purified using the SUPERPURE PLUS cartridge method described in Example 5 for the detection of two alleles of a SNP directly from genomic DNA. In particular, this example demonstrates that oligonucleotides purified by virtue of the presence of a 3' terminal lipophilic moiety are suitable for detecting SNPs directly from as little as 60 ng of genomic DNA.

Genomic DNA Extraction

Genomic DNA was isolated from 5 mls of whole blood and purified using the Autopure, manufactured by Gentra Systems, Inc. (Minneapolis, Minn.). The purified DNA was in 500 μl of dH$_2$O.

INVADER Assay Reactions

Probe oligonucleotides with SEQ ID NOs: 27 and 28 containing C$_{16}$ moieties, synthesized as described in Examples 1 and 2 and purified as described in Example 5 using 0.5 ml 25% acetonitile/65% water+1% Tween-20 to elute the probe oligonucleotides from the SUPERPURE PLUS column, were used in INVADER assays to detect db SNP ID rs2295520 in genomic DNA isolated from blood.

INVADER reactions on genomic DNA targets were set up in a 384-well microtiter plate containing 32 ng of CLEAVASE XI, a RED FRET cassette (5' (red dye) tct (Z28) tcg gcc ttt tgg ccg aga gac ctc ggc gcg (hexanediol)-3'[SEQ ID NO:22]), and a FAM FRET cassette (5' (fam) tct (Z28) agc cgg ttt tcc ggc tga gag tct gcc acg tca t (hexanediol) [SEQ ID NO: 23]), each at a final concentration of 0.25 μM.

For the test samples, 3 μl of genomic DNA containing a total of 240 ng, 120 ng, or 60 ng were added to the appropriate wells. For the no target controls, 3 μl of tRNA at a concentration of 10 ng/μl were added in lieu of target. 3 μl of a master mix of primary probes 5'-CGCGCCGAGGCCACACTTGA-CATGCC-3' (SEQ ID NO: 27) and 5'-ATGACGTGGCA-GACGCACACTTGACATGCC-3' (SEQ ID NO:28), INVADER oligonucleotide (5'-GGGTGTAAAAGCAG-CAGGTGTGTGTGTATGCTTT-3' [SEQ ID NO:29]), MOPS, and MgCl$_2$, was added so that each reaction contained the following (final concentrations): 10 mM MOPS, pH 7.5, 7.5 mM MgCl$_2$, 0.5 µM each primary probe, and 0.05 µM INVADER oligonucleotide.

Figure 7A:
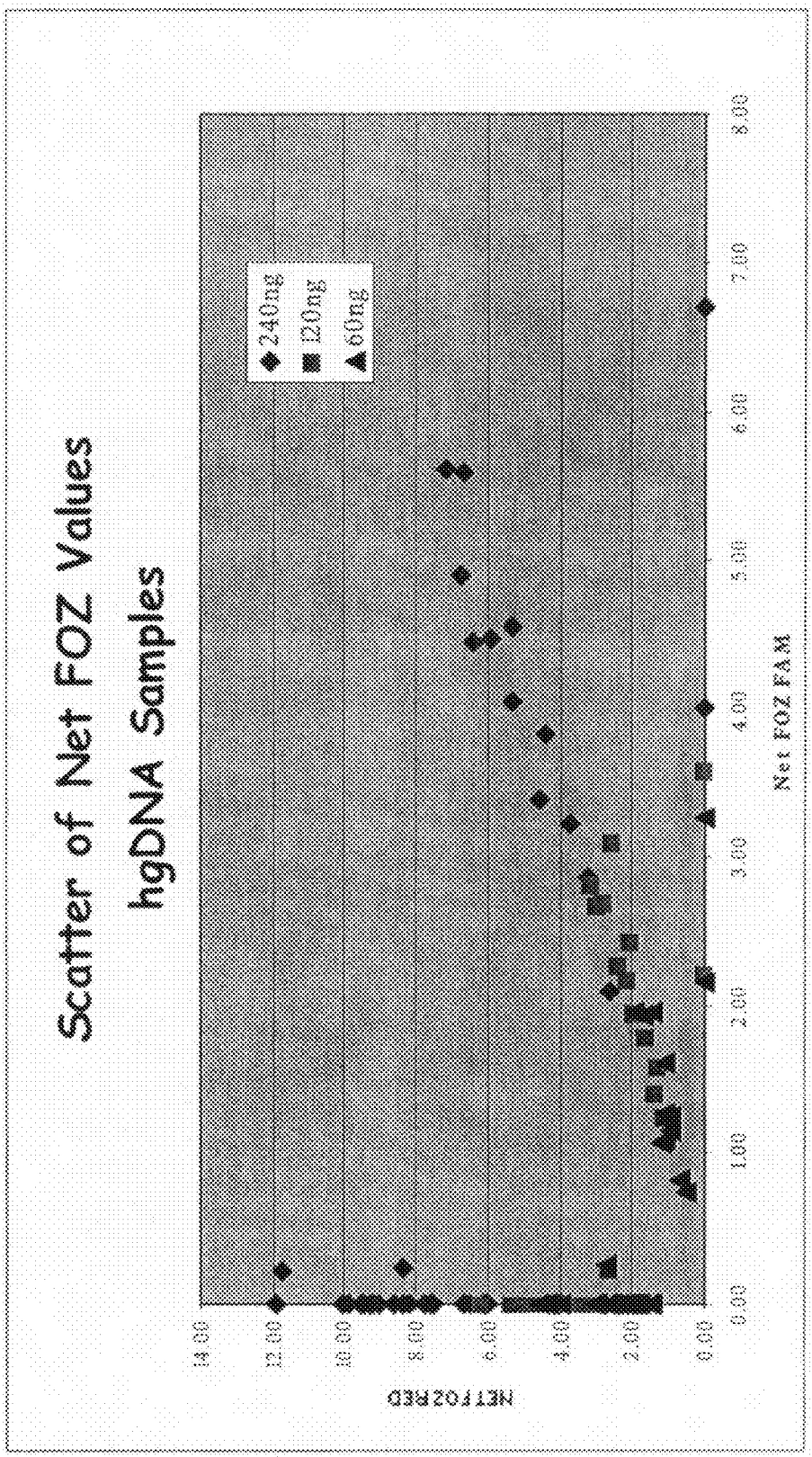
FIG. 7 shows the results of assays to detect a SNP directly from genomic DNA with C16 3' end tagged probe oligonucleotides purified by cartridge purification.
Figure 7B:
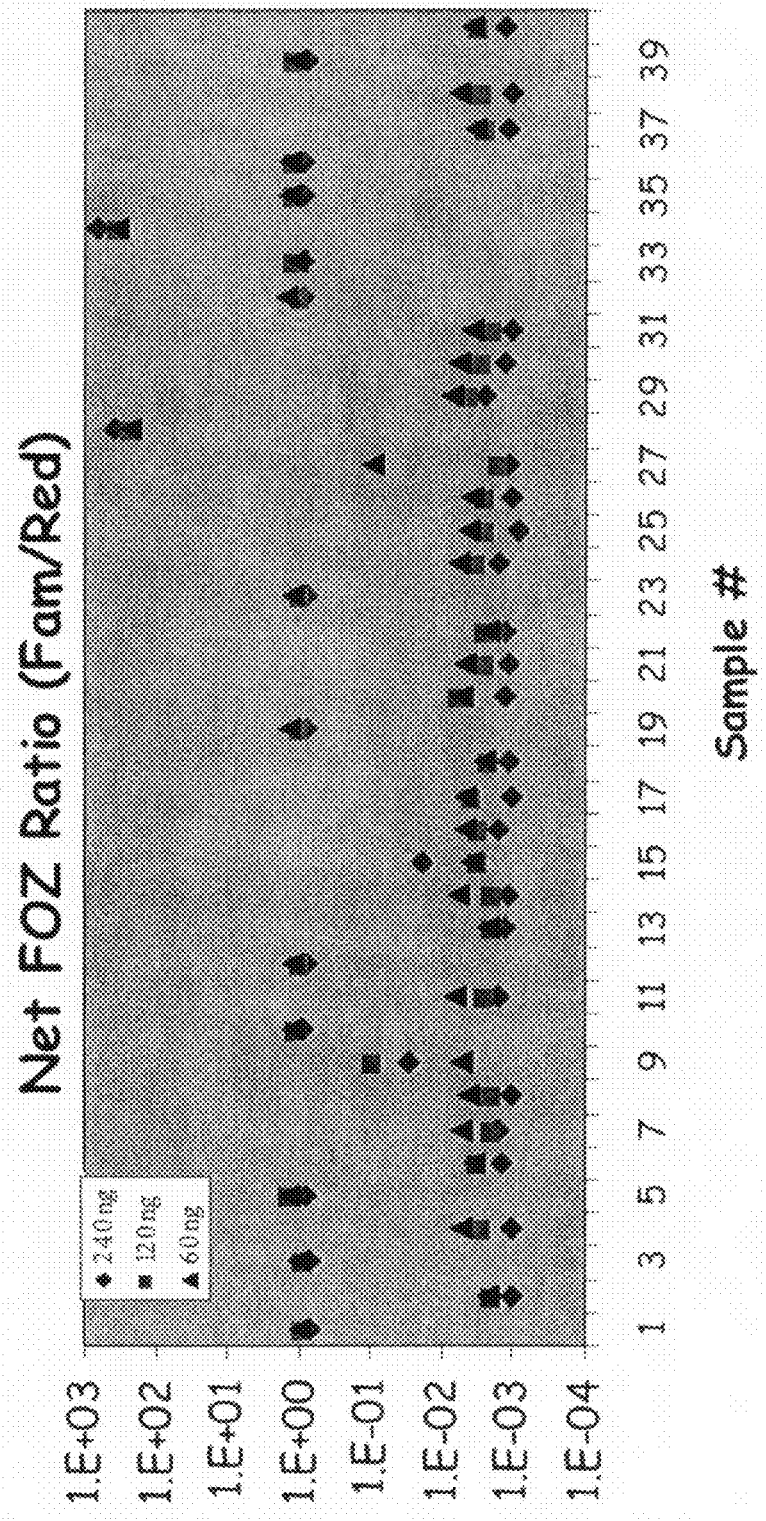

The reactions were covered with 6 µl of mineral oil and incubated at 95° C. for 5 minutes then cooled to 63° C. Fluorescence signal was read after 4 hours of incubation at 63° C. FIG. 7A presents the INVADER assay results obtained from each target and indicates that the genomic samples gave values of net FOZ, where FOZ is calculated as described in Example 3 and where Net FOZ=FOZ−1. FIG. 7B compares the ratios of the two FOZ values (i.e. wild type and mutant) for each sample. The Net FOZ values were used to calculate the WT:Mut Ratio as follows:

$$\text{Ratio} = \frac{(\text{Net WT } FOZ)}{(\text{Net Mut } FOZ)}$$

These data demonstrate that oligonucleotides with 3' end C$_{16}$ groups and purified by the method of Example 5 can be used as Probe oligonucleotides for the discrimination of SNPs directly from genomic DNA. This example also demonstrates that probe oligonucleotides purified by the method of Example 5 can detect SNPs from as little as 60 ng of genomic DNA, which is comparable to the capabilities of probe oligonucleotides purified by ion exchange HPLC.

EXAMPLE 7

Relationship Between Target Concentration and Level of Probe Oligonucleotide Purity in the Invader Assay This example describes the relationship between the amount of target nucleic acid included in the INVADER reaction and the level of purity needed in the INVADER assay. This example provides hypothetical experiments in which various levels of contaminating shrapnel within a preparation of primary probe molecules are added to INVADER reactions containing various levels of target molecules. The results of these contemplated experiments predict that detection of high target levels will be unaffected by relatively high levels of shrapnel, while detection of low target levels may be compromised by small quantities of shrapnel.

The kinetics of signal accumulation in the INVADER assay may, for example, be described by the following equation from Hall, J. et al., Proc. Natl. Acad. Sci. 97: 8272-7 (2000), herein incorporated by reference.

$$[S]=½α_1α_2[T]t^2+k_bt$$

where S=signal or cleaved FRET probe, $α_1$ is the cleavage rate of the primary invasive cleavage reaction, $α_2$ is the cleavage rate of the secondary invasive cleavage reaction, T is the amount of target in the reaction, t is time, $k_b$ is the rate of background generation which does not change during the time of the reaction. $k_b$ is a constant that does not change with respect to time.

Using this equation, it is possible to contemplate the effect of background generation resulting from the inclusion of probe fragments lacking intact 3' ends (e.g. shrapnel on INVADER reactions to which various levels of target nucleic acid have been added). For all hypothetical examples, we make the following assumptions: primary and secondary cleavage rates of 15 cleavages per target per minute [Hall, J. et al., Proc. Natl. Acad. Sci. 97: 8272-7 (2000)] and a cleavage rate for the background reaction including shrapnel of approximately 0.1× that of the reaction including intact primary probe, based on the likelihood that such molecules contain 3' terminal phosphate moieties. INVADER oligonucleotides containing a 3' terminal phosphate decrease cleavage rate by at least 10-fold [Kaiser, M. W. et al., J. Biol. Chem. 274: 21387-21394 (1999), hereby incorporated by reference]. In each case, the starting concentrations of primary probe and FRET probe are 0.5 µM and 0.25 µM, respectively. In a 10 µl reaction, these concentrations give a total of primary probe molecules of 3×10$^{12}$ and 1.5×10$^{12}$ FRET probe molecules.

By contemplating various levels of shrapnel molecules in a primary probe population, e.g. 2%, 1%, 0.5%, 0.05%, and 0.01%, we can examine the effects on INVADER reactions containing various levels of target molecules.

In the case of monoplex PCR reactions, a typical amount of target molecules added to an INVADER reaction is approximately 10$^7$. INVADER reactions containing such target levels are typically run for 15 to 30 minutes. FIG. 8A shows the theoretical percentage of FRET probe cleaved, i.e. S as a function of time in the INVADER reaction. The overlaid straight lines represent the accumulation of cleaved FRET probe with time based on different percentages of shrapnel. Clearly, in the case of these high target levels, even the maximum amount of shrapnel fails to interfere with generation of the cleaved FRET probe, and thus of signal, over the time of the reaction.

FIG. 8b shows the theoretical effects of various shrapnel levels on the detection of intermediate levels of target, i.e. 10$^6$ target molecules, such as might be obtained for each target in a highly multiplexed PCR reaction. In this case, the highest shrapnel levels contemplated, i.e. 0.5, 1, and 2%, generate more cleaved FRET probe in the initial time points than does the target-specific INVADER reaction such that all of the available FRET probe is cleaved in non-specific reactions. At 0.25% shrapnel, there is a point at which the target-specific reaction overtakes the background reaction. However, at this point, the majority of the FRET probe, i.e. ~75%, is already depleted by the non-specific reaction. At shrapnel levels of 0.1% and below, cleaved FRET probe generated by the target-specific reaction exceeds that from the background reaction such that this amount of shrapnel contamination in a population of primary probes does not interfere with detection by the INVADER assay.

Figure 8C:
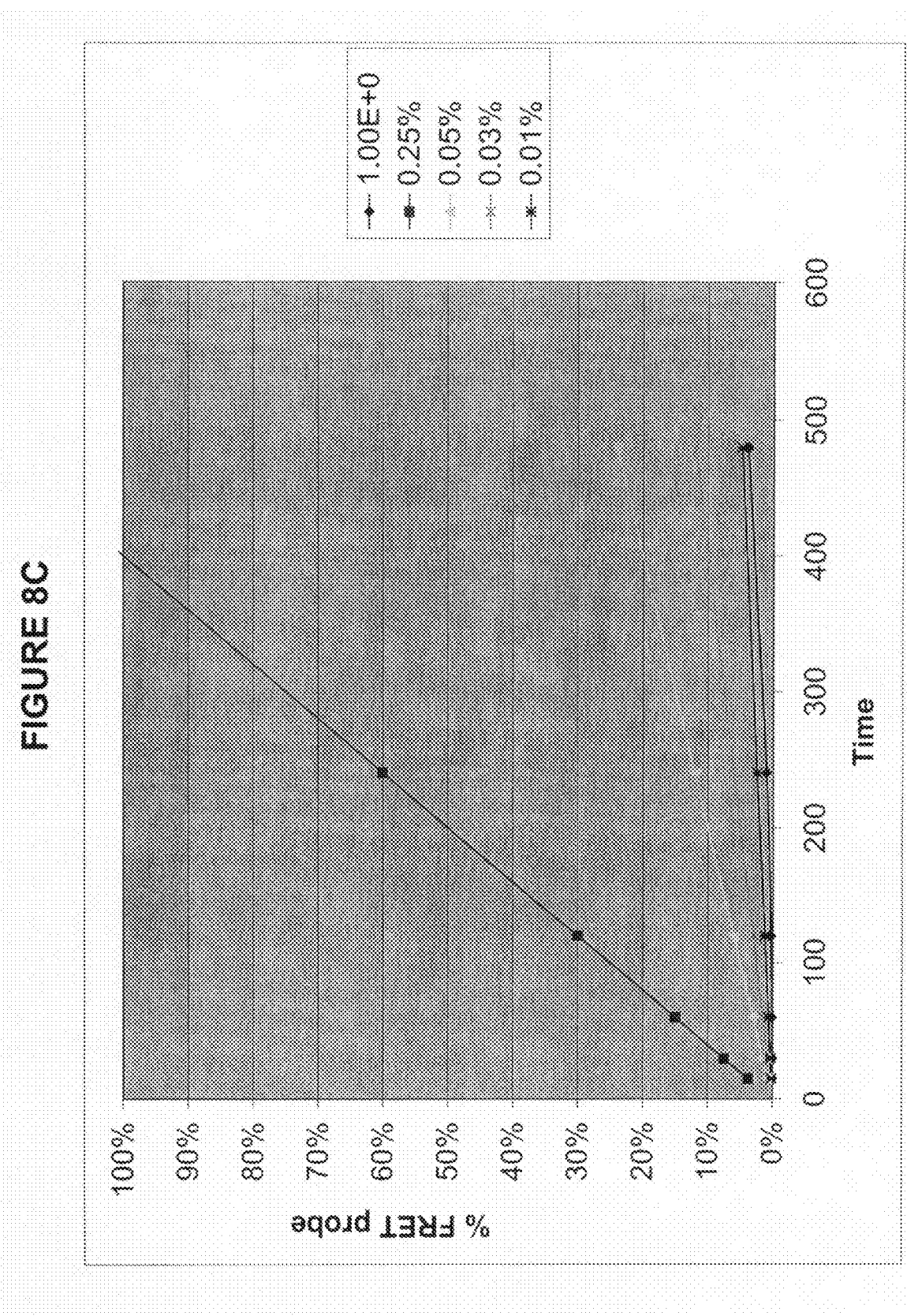
FIG. 8 shows the predicted extent of FRET probe cleavage resulting from various levels of shrapnel contamination of primary probe populations vs. FRET probe cleavage resulting from target-specific INVADER assay cleavage at various target levels.

FIG. 8C shows the theoretical effects of various shrapnel levels on the detection of relatively low levels of target, i.e. 3×10$^4$ target molecules, corresponding to 100 ng of genomic DNA, i.e. the amount of genomic DNA typically added to a 10 µl reaction (see Example 6). In this case, all but the lowest level of shrapnel contemplated, i.e. 0.01%, results in background cleavage of FRET probe that greatly exceeds that generated in the target-dependent reaction such that levels of contamination>0.01% interferes with detection by the INVADER assay.

This example illustrates the importance of removing shrapnel contamination from primary probe preparations to be used for detecting low target levels, such as genomic DNA. This example further illustrates that detection of high target levels, e.g. from monoplex PCR reactions, is unaffected by even relatively high levels of shrapnel.

EXAMPLE 8

Affinity Purification of Probe Oligonucleotides Containing a 3' Poly A Tail

This example describes the use of poly dA: oligo dT affinity interactions as a means of purifying oligonucleotides for use as probes in INVADER reactions. In particular, this example describes the inclusion of 9 A residues at the 3' terminus of the oligonucleotides and the purification of these oligonucleotides based on their adherence to oligo dT cellulose. As the results below demonstrate, the inclusion of 3' terminal poly A sequences does not inhibit the INVADER reaction. These experiments further illustrate that 3' end affinity purification based on poly dA: oligo dT affinity (or any other type of sequence specific affinity) may be used to generate oligonucleotide compositions that are preferable to unpurified oligonucleotide preparations for use in the INVADER assay.

Purification of Probe Oligonucleotides

In this example, SEQ ID NOs:30 (5'-CGCGCCGAGGT-GCTGTGTCCAT GGAAAAAAAAAA-hexanediol-3') and 31 (5'-ATGACGTGGCAGACCGCT GTGTCCATG-GAAAAAAAAA-hexanediol-3') were employed as probe oligonucleotides for use in INVADER assays to detect wild type and variant versions of SNP rs381320 (dbSNP ID).

For each of these sequences, the 5' portion ("flap") is highlighted with underlining. The italicized region comprises the poly A tail. The remaining non-underlined part of the sequences is the 3' portion (Target Specific Region). Also, fragments that would be generated during an invasive cleavage reaction with these sequences (and the indicated INVADER oligonucleotides shown in the following Examples) are the underlined sequence (5' portion) plus the first base (in bold) from the 3' portion. These fragments are designed to participate in a second invasive cleavage reaction with a FRET cassette by serving as the INVADER (upstream) oligonucleotide in this second invasive cleavage reaction.

These oligonucleotides (SEQ IDs:30 and 31) were synthesized in 1 µmol scale on the PerSeptive Biosystems Expedite 8909 automated DNA synthesizer using the standard phosphoramidite coupling protocol with DMT off. Cleavage (off CPG) and deprotection was performed with ammonium hydroxide in a final volume of 500 µl overnight at 55° C. Oligonucleotide preparations were filtered through a 0.2 µm teflon acrodisk and dried in a speedvac. Probe oligonucleotides containing the poly A tails were used in INVADER assays either unpurified or following purification on an oligo dT column. Unpurified, or "crude", probe oligonucleotide preparations were suspended in Te buffer (10 mM Tris-HCl, pH 8.0, 0.1 mM EDTA) at a concentration of 1 mM and added to INVADER reactions as described below.

Aliquots of the "crude" oligonucleotide preparations were diluted 1:10 in oligo dT cellulose binding buffer (0.5 M NaCl, 10 mM MOPS, pH 7.5, 0.2% Tween-20, 0.1 mM EDTA). 200 µl of each of two aliquots of diluted oligonucleotides (SEQ IDs:30 and 31) were loaded onto an oligo dT spin column prepared as follows: 1 g of oligo dT cellulose (Ambion, Austin, Tex., catalog no. 10020-1 g) was dissolved in 6 mls of oligo dT cellulose binding buffer, and aliquots of 400 µl were loaded into CoStar Spin-X columns (Corning, Inc. Corning, N.Y., catalog no. 8161). For each SEQ ID:30 and 31, one column was eluted with 100 µl dH20 directly ("no-wash prep") and one was washed three times with oligo dT binding buffer 200 µl and then eluted with 100 µl of $dH_2O$ ("washed prep").

Genomic DNA Extraction

Genomic DNA was isolated from 5 mls of whole blood and purified using the Autopure, manufactured by Gentra Systems, Inc. (Minneapolis, Minn.). The purified DNA was in 500 µl of $dH_2O$.

PCR Amplification of Genomic DNA

Target DNA was provided as a PCR product using 5'-TG-CAGGCTGCCTTACAG ACC-3' (SEQ ID NO:25) as a forward primer and 5'-CTGCTTGAAGCTGCCCAGGAA-3' (SEQ ID NO:26) as a reverse primer. PCR reactions were multiplexed to amplify 48 distinct regions. Reaction mixtures contained the following final concentrations in a volume of 50 µl:100 mM Tris, pH 7.5, 50 mM KCl, 1.5 mM $MgCl_2$, 200 µM each dNTP, 25 nM each primer, 2.5 units µl QIAGEN HotStarTaq DNA polymerase, and 30 ng genomic DNA. PCR reactions were incubated at 95° C. for 15 minutes, then run for 35 cycles of 94° C. for 30 seconds, 55° C. for 1 minute. PCR products were diluted 1:25 prior to inclusion in the INVADER assay.

Biplex INVADER Reactions

Biplex INVADER reactions (e.g. as shown in FIG. 1) were carried out in a final volume of 6 µl in a 384-well microplate containing the following reagents dried down directly in the microplate wells: 60 ng/reaction of the CLEAVASE VIII enzyme (Third Wave Technologies, Madison, Wis.) and FRET oligonucleotides (fam) tct (Z28) agc cgg ttt tcc ggc tga gag tct gcc acg tca t-hexanediol (SEQ ID NO:23) (FAM) and (red dye) tct (Z28) tcg gcc ttt tgg ccg aga gac ctc ggc gcg-hexanediol (SEQ ID NO:22) (RED) at a final concentration of 0.25 µM each. A 3 µl volume containing the following reagents (all concentrations specified are final concentrations): primary probes (SEQ IDs NO:30 and 31), 0.5 µM each; INVADER oligonucleotide (upstream oligonucleotide) 5'-GGCTTAAGGTCACAGGTCCAAGA AAGCCCA-3' (SEQ ID NO:24), 0.05 µM, 10 mM MOPS, and 15 mM $MgCl_2$.

Subsequently, 3 µl of diluted PCR product (target sequence) were added, and the reactions were covered with 6 µl mineral oil. For the no target controls, 3 µl of tRNA at a concentration of 10 ng/µl were added in lieu of target. Plates were sealed and incubated at 95° C. for 5 minutes to denature the target, then cooled to the reaction temperature of 63° C. Fluorescence signal was read after 40 minutes in a CytoFluor® 4000 fluorescence plate reader (Applied Biosystems, Foster City, Calif.). The settings used were: 485/20 nm excitation/bandwidth and 530/25 nm emission/bandwidth for F dye detection, and 560/20 nm excitation/bandwidth and 620/40 nm emission/bandwidth for R dye detection. The instrument gain was set for each dye so that the No Target Blank produced between 100-200 Absolute Fluorescence Units (AFUs).

The raw data that is generated by the device/instrument is used to measure the assay performance (real-time or endpoint mode). The equations below provide how FOZ, and other values are calculated. NTC in the equations below represents the signal from the No Target Control. Also, FOZ is an abbreviation for fold over zero. Net FOZ is calculated by subtracting 1 from FOZ to eliminate contribution from background signal.

FOZ or Signal/No Target $$FOZ_{Dye1} = (RawSignal_{Dye1}/NTC_{Dye1}).$$

$$FOZ_{Dye2} = (RawSignal_{Dye2}/NTC_{Dye2})$$

The two FOZ values (i.e. wild type and mutant) for each sample were used to calculate the WT:Mut Ratio as follows:

$$Ratio = \frac{(Net\ WT\ FOZ)}{(Net\ Mut\ FOZ)}$$

where Net FOZ=FOZ−1

In the case of replicated runs, $RawSignal_{DyeX}$ and $NTC_{DyeX}$ are the averaged values.

Figure 9A:
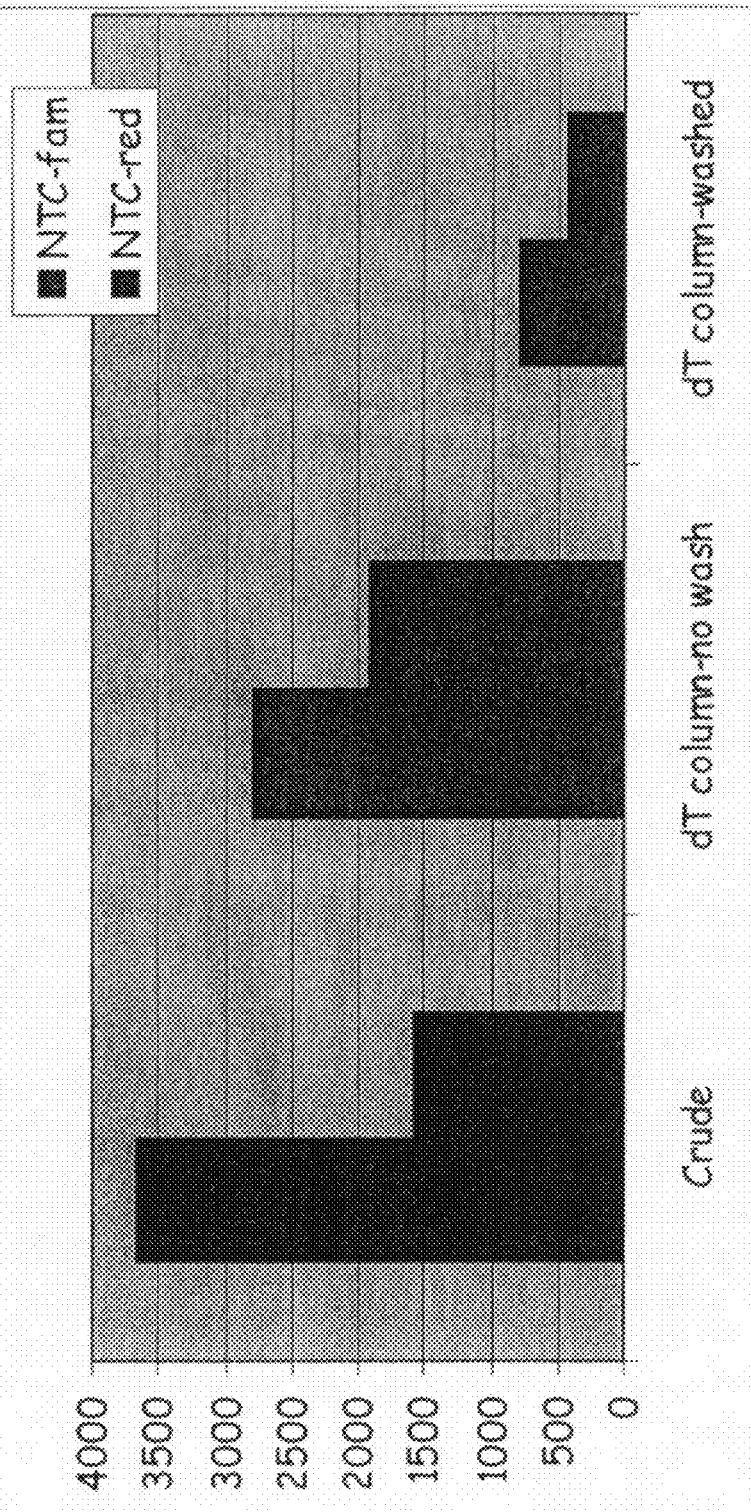
FIG. 9 shows the results of assays to detect a SNP with probe oligonucleotides containing poly dA tails purified by their affinity for oligo dT cellulose.
Figure 9B:
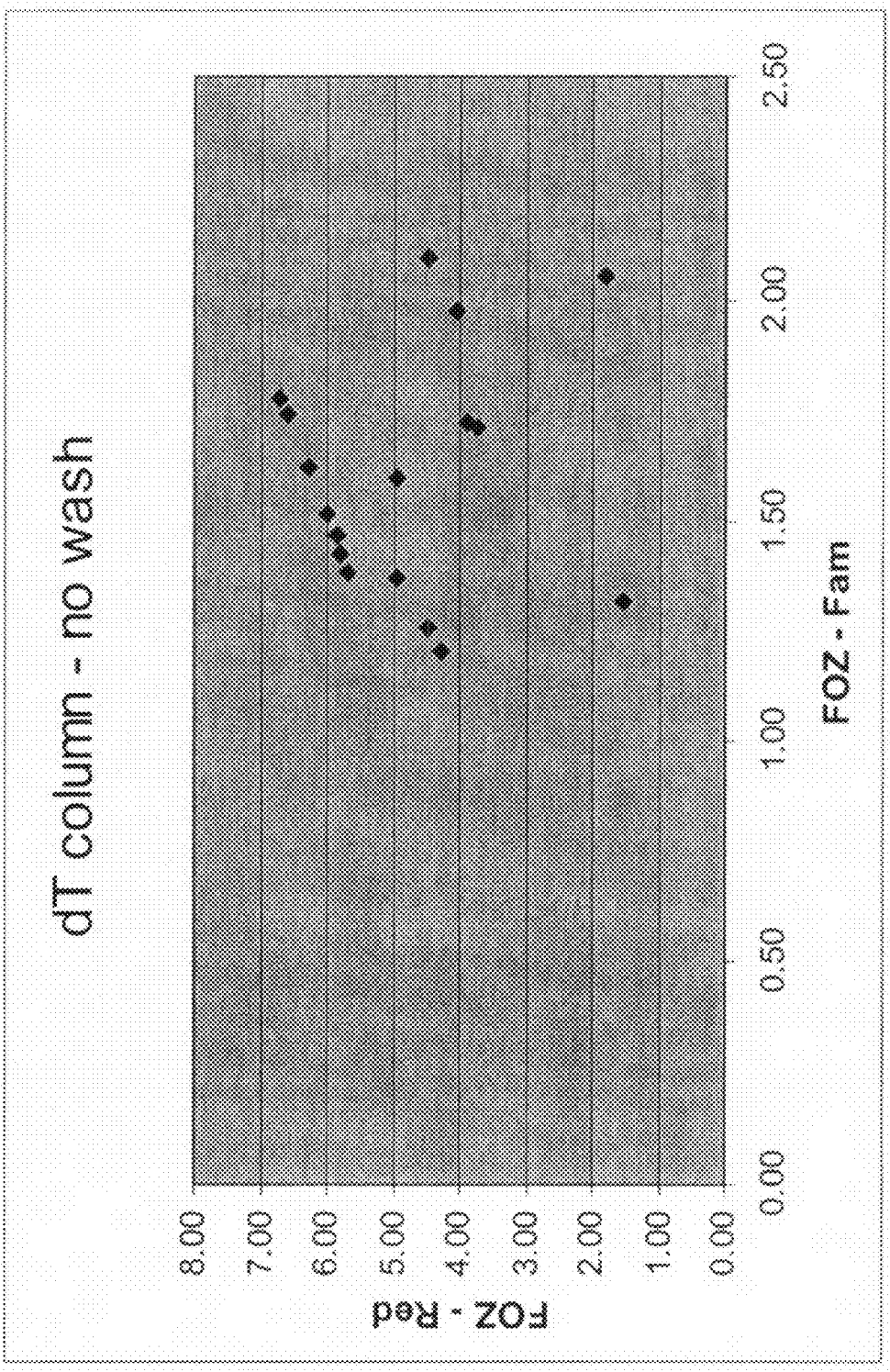
Figure 9C:
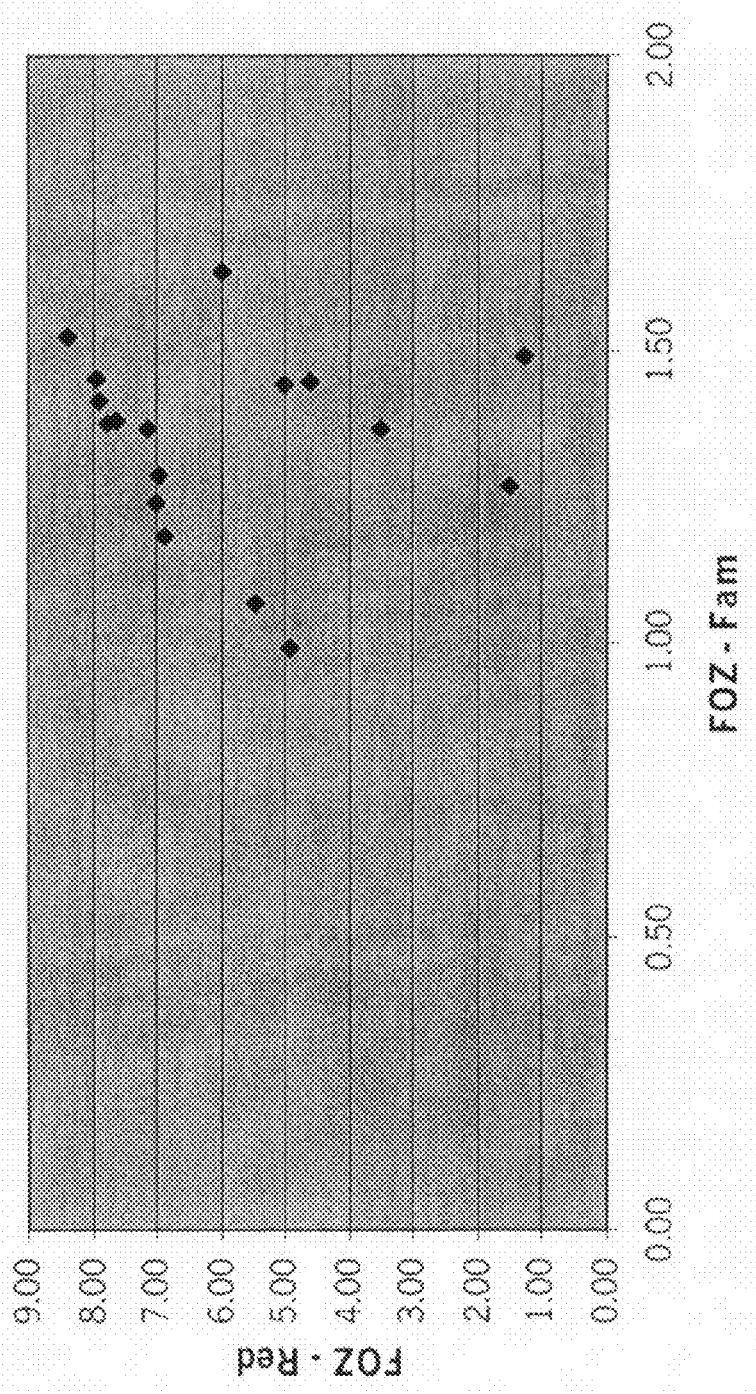

FIG. 9 presents the results of INVADER assays conducted to compare the performance of crude, unwashed, and washed preparations of probe oligonucleotides purified based on 3' poly dA: oligo dT affinity. FIG. 9A includes the results of no target control (NTC) INVADER assays. Poly A: oligo dT purification decreased non-specific background signal generation in the NTC INVADER assays. Washing the columns prior to elution of the probe oligonucleotides reduced the generation of background signal by approximately four-fold. Accordingly, the INVADER assay results from reactions including target presented in FIGS. 9B-D indicate that differentiation of samples according to genotype is possible only when the crude oligonucleotide preparations are purified by binding to the oligo dT column and washed prior to elution. In FIG. 9D, "X" indicates homozygotes reporting to RED dye, circles indicate heterozygotes, and triangles, homozygotes reporting to FAM dye.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A method of producing a preparation of oligonucleotides having a reduced number of 5' oligonucleotide fragments, comprising;
   a) providing a solid support comprising a plurality of affinity groups;
   b) synthesizing a plurality of oligonucleotides in the 3' to 5' direction such that the 3' ends of said oligonucleotides are attached to said affinity groups;
   c) while said 3' ends of said plurality of oligonucleotides remain attached to said solid support via said affinity groups, treating said oligonucleotides with an agent that cleaves oligonucleotides at abasic sites, such that oligonucleotides containing abasic sites are cleaved, to produce a mixture of 5' oligonucleotide fragments, 3' oligonucleotide fragments, and uncleaved oligonucleotides;
   d) separating said 5' oligonucleotide fragments from said solid supports attached to 3' oligonucleotides fragments and said uncleaved oligonucleotides;
   e) cleaving said uncleaved oligonucleotides and 3' oligonucleotide fragments from said solid support to generate a mixture comprising a plurality of released uncleaved oligonucleotides and 3' oligonucleotide fragments comprising 3' end affinity groups and lacking abasic sites; and
   f) purifying said plurality of released uncleaved oligonucleotides and 3' oligonucleotide fragments employing said 3' end affinity groups to generate a preparation of oligonucleotides having a reduced number of 5' oligonucleotide fragments.

2. The method of claim 1, wherein said solid support comprises controlled pore glass.

3. The method of claim 1, wherein said plurality of affinity groups comprise lipophilic moieties.

4. The method of claim 1, wherein said affinity groups comprise long-chain polycarbon linkers.

5. The method of claim 4, wherein said long-chain polycarbon linker comprises $C_{16}$ or $C_{14}$.

6. The method of claim 1, wherein said agent comprises aqueous lysine.

* * * * *

SEQUENCE LISTING

```
<160> NUMBER OF SEQ ID NOS: 31

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
cgcgccgagg acctttggaa gcttgtat                                          28

<210> SEQ ID NO 2
<211> LENGTH: 28
<212> TYPE: DNA
<213> ORGANISM: Artificial Sequence
<220> FEATURE:
<223> OTHER INFORMATION: Synthetic

<400> SEQUENCE: 2
acggacgcgg aggcctttgg aagcttgt                                          28

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
cgcgccgagg atgacatgat tactgagagt t                                      31

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
```
acggacgcgg aggtgacatg attactgaga gt                                    32

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggaatgccgt cttggaagcc                                                  20

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
cccggcttac cttatagacc acc                                              23

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
aacatgttcc tggtgctgat attctca                                          27

<210> SEQ ID NO 8
<211> LENGTH: 29
<212> TYPE: DNA
<213> ORGANISM: Artificial Sequence
<220> FEATURE:
<223> OTHER INFORMATION: Synthetic

<400> SEQUENCE: 8
cacctgtaag ggtgatgtca tcatcatca                                        29

<210> SEQ ID NO 9
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quenching group.

<400> SEQUENCE: 9
tctagccggt tttccggctg agacctcggc gcg                                   33

<210> SEQ ID NO 10
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28 quenching group.

<400> SEQUENCE: 10
tctagccggt tttccggctg agactccgcg tccg                34

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
cagcgatggt cgtgccagtt ttccggt                27

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
cggtctagcc tgtgtggaag agcccat                27

<210> SEQ ID NO 13
<211> LENGTH: 35
<212> TYPE: DNA
<213> ORGANISM: Artificial Sequence
<220> FEATURE:
<223> OTHER INFORMATION: Synthetic

<400> SEQUENCE: 13
acggacgcgg aggattaggg tttgacttat atgtg                35

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
cgcgccgagg aattagggtt tgacttatat gtg                33

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
ggttccctga gagttcccag cc                22

<210> SEQ ID NO 16
<211> LENGTH: 26
<212> TYPE: DNA
<213> ORGANISM: Artificial Sequence
<220> FEATURE:
<223> OTHER INFORMATION: Synthetic

<400> SEQUENCE: 16
cagaggcttg ggatggtaat actcac                26

```
<210> SEQ ID NO 17
<211> LENGTH: 38
<212> TYPE: DNA
<213> ORGANISM: Artificial Sequence
<220> FEATURE:
<223> OTHER INFORMATION: Synthetic

<400> SEQUENCE: 17
cctttctctc tccagtccac agaatcaggc aatatcct                            38

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
cgcgccgagg tgctgtgtcc atgga                                          25

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
atgacgtggc agaccgctgt gtccatgg                                       28

<210> SEQ ID NO 20
<211> LENGTH: 50
<212> TYPE: DNA
<213> ORGANISM: Artificial Sequence
<220> FEATURE:
<223> OTHER INFORMATION: Synthetic

<400> SEQUENCE: 20
cggttccatg gacacagcag ggctttcttg gacctgtgac cttaagccca               50

<210> SEQ ID NO 21
<211> LENGTH: 50
<212> TYPE: DNA
<213> ORGANISM: Artificial Sequence
<220> FEATURE:
<223> OTHER INFORMATION: Synthetic

<400> SEQUENCE: 21
cggttccatg gacacagcgg ggctttcttg gacctgtgac cttaagccca               50

<210> SEQ ID NO 22
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quenching group.

<400> SEQUENCE: 22
tcttcggcct tttggccgag agacctcggc gcg                                 33

<210> SEQ ID NO 23
<211> LENGTH: 37
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a
      Z28 quenching group.

<400> SEQUENCE: 23
tctagccggt tttccggctg agagtctgcc acgtcat                              37

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
ggcttaaggt cacaggtcca agaaagccca                                      30

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
tgcaggctgc cttacagacc                                                 20

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
ctgcttgaag ctgcccagga a                                               21

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
cgcgccgagg ccacacttga catgcc                                          26

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
atgacgtggc agacgcacac ttgacatgcc                                      30

<210> SEQ ID NO 29
<211> LENGTH: 34
<212> TYPE: DNA
<213> ORGANISM: Artificial Sequence
```

```
<220> FEATURE:
<223> OTHER INFORMATION: Synthetic

<400> SEQUENCE: 29
gggtgtaaaa gcagcaggtg tgtgtgtatg cttt                             34

<210> SEQ ID NO 30
<211> LENGTH: 34
<212> TYPE: DNA
<213> ORGANISM: Artificial Sequence
<220> FEATURE:
<223> OTHER INFORMATION: Synthetic

<400> SEQUENCE: 30
cgcgccgagg tgctgtgtcc atggaaaaaa aaaa                             34

<210> SEQ ID NO 31
<211> LENGTH: 37
<212> TYPE: DNA
<213> ORGANISM: Artificial Sequence
<220> FEATURE:
<223> OTHER INFORMATION: Synthetic

<400> SEQUENCE: 31
atgacgtggc agaccgctgt gtccatggaa aaaaaaa                          37
```